United States Patent
Cheng et al.

(10) Patent No.: US 12,258,424 B2
(45) Date of Patent: Mar. 25, 2025

(54) POLYPEPTIDES AND COMPOSITIONS COMPRISING THE SAME

(71) Applicants: Kun Cheng, Kansas City, MO (US); Hao Liu, Kansas City, MO (US); John Fetse, Kansas City, MO (US); Umar-Farouk Mamani, Kansas City, MO (US)

(72) Inventors: Kun Cheng, Overland Park, KS (US); Hao Liu, Rockville, MD (US); John Fetse, Mission, KS (US); Umar-Farouk Mamani, Mission, KS (US)

( * ) Notice: Subject to any disclaimer, the term of this patent is extended or adjusted under 35 U.S.C. 154(b) by 0 days.

(21) Appl. No.: 17/507,301

(22) Filed: Oct. 21, 2021

(65) Prior Publication Data

US 2022/0119451 A1   Apr. 21, 2022

Related U.S. Application Data

(60) Provisional application No. 63/104,256, filed on Oct. 22, 2020, provisional application No. 63/094,653, filed on Oct. 21, 2020.

(51) Int. Cl.
*C07K 7/08* (2006.01)
*A61K 38/00* (2006.01)
*C07K 7/06* (2006.01)

(52) U.S. Cl.
CPC ............ *C07K 7/08* (2013.01); *C07K 7/06* (2013.01); *A61K 38/00* (2013.01)

(58) Field of Classification Search
None
See application file for complete search history.

(56) References Cited

FOREIGN PATENT DOCUMENTS

CN        106749527 A  *  5/2017

OTHER PUBLICATIONS

Liu et al. (Journal for Immuno Therapy of Cancer (2019) 7:270) (Year: 2019).*
FITF guidance (downloaded from URL:<Microsoft PowerPoint—FITF Comp Exr Trng 102(a)(1) and (a)(2) 6-18 with talking points FINAL>). (Year: 2018).*
Costello et al. (Pancreat Disord Ther; Suppl 4; doi: 10.4172/2165-7092.S4-002) (Year: 2013).*
GenBank (class I SAM-dependent methyltransferase [Neobacillus pocheonensis], MCM2534700.1) (Year: 2020).*
Chen, Z. et al. "Discovery of Aptamer Ligands for Hepatic Stellate Cells Using SELEX", Theranostics, vol. 7, Issue 12, pp. 2982-2995 (Jul. 21, 2017).
Chang, H-N., et al. Blocking of the PD-1/PD-L1 Interaction by a d-Peptide Antagonist for Cancer Immunotherapy, Angew. Chem. Int. Ed., vol. 54, pp. 11760-11764 (Aug. 10, 2015).
Dong, H., et al. "Tumor-associated B7-H1 promotes T-cell apoptosis: A potential mechanism of immune evasion", Nature medicine, vol. 8, No. 8, pp. 793-800 (Aug. 2002).
Freeman, G. J., et al., "Engagement of the PD-1 Immunoinhibitory Receptor by a Novel B7 Family Member Leads to Negative Regulation of Lymphocyte Activation", Journal of experimental medicine, vol. 192, No. 7, pp. 1027-1034 (Oct. 2, 2000).
Herbst, R. S., et al., "Predictive correlates of response to the anti-PD-L1 antibody MPDL3280A in cancer patients", Nature, vol. 515, pp. 563-567 (Nov. 27, 2014).
Mace, T. A., et al., "IL-6 and PD-L1 antibody blockade combination therapy reduces tumour progression in murine models of pancreatic cancer", Gut, pp. 320-332 (Feb. 2018).
Park, S., et al., "Micromolar affinity CAR T cells to ICAM-1 achieves rapid tumor elimination while avoidingsystemic toxicity", Scientific reports, pp. 1-15 (Oct. 30, 2017).
Zak, K. M., et al., "Structure of the Complex of Human Programmed Death 1, PD-1, and Its Ligand PD-L1", Structure 23, pp. 2341-2348 (Dec. 1, 2015).

* cited by examiner

*Primary Examiner* — Sergio Coffa
(74) *Attorney, Agent, or Firm* — SHOOK, HARDY & BACON L.L.P.

(57) ABSTRACT

Polypeptides and compositions having the polypeptides. Methods for treating cancer utilizing polypeptides and compositions having the polypeptides. The polypeptides can bind to human PD-L1 protein. The polypeptides can block the PD-1/PD-L1 interaction.

16 Claims, 30 Drawing Sheets
(9 of 30 Drawing Sheet(s) Filed in Color)
Specification includes a Sequence Listing.

```
                      SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Synthesized

<400> SEQUENCE: 1

His Tyr Pro Phe Arg Pro His Ala Asn Gln Ala Ser
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthesized
```

```
<400> SEQUENCE: 2

Trp His Arg Ser Tyr Tyr Thr Trp Asn Leu Asn Thr
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthesized

<400> SEQUENCE: 3

Trp His Phe Ser Tyr Asn Trp Arg Trp Leu Pro Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthesized

<400> SEQUENCE: 4

Asp Tyr His Asp Pro Ser Leu Pro Thr Leu Arg Lys
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: DISULFID
<222> LOCATION: (1)..(12)

<400> SEQUENCE: 5

Cys His Arg Ser Tyr Tyr Thr Trp Asn Leu Asn Cys
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthesized
<220> FEATURE:
<221> NAME/KEY: DISULFID
<222> LOCATION: (1)..(7)

<400> SEQUENCE: 6

Cys His Arg Ser Tyr Tyr Cys Trp Asn Leu Asn Thr
1               5                   10

<210> SEQ ID NO 7
<211> LENGTH: 9
<212> TYPE: PRT
<213> ORGANISM: Artificial Sequence
<220> FEATURE:
<223> OTHER INFORMATION: Synthesized

<400> SEQUENCE: 7

Trp His Arg Ser Tyr Tyr Thr Trp Asn
1               5
```

POLYPEPTIDES AND COMPOSITIONS COMPRISING THE SAME

CROSS-REFERENCE TO RELATED APPLICATIONS

This application claims priority to U.S. provisional application No. 63/094,653, filed on Oct. 21, 2020, and entitled "Polypeptides and Compositions Comprising the Same;" and to U.S. provisional application No. 63/104,256, filed on Oct. 22, 2020, and entitled "Polypeptides and Compositions Comprising the Same." The contents of each of the above-referenced applications are incorporated by referenced herein in their entireties.

STATEMENT REGARDING FEDERALLY SPONSORED RESEARCH OR DEVELOPMENT

This invention was made with government support under grant numbers R01 CA231099 and R01AA021510 awarded by National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Oct. 20, 2020, is named 377333_SEQ_LISTING_10-20-2021_ST25.txt and is 1869 bytes in size.

FIELD OF THE INVENTION

The present disclosure relates to polypeptides and compositions comprising the same. More particularly, the present disclosure relates to polypeptides and compositions comprising the same where the polypeptides can interact with PD-L1 proteins.

BACKGROUND

Immunotherapy using checkpoint inhibitors, especially PD-1/PD-L1 inhibitors, has now evolved into the most promising therapy for cancer patients. However, most of these inhibitors are monoclonal antibodies, and their large size may limit their tumor penetration, leading to suboptimal efficacy.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
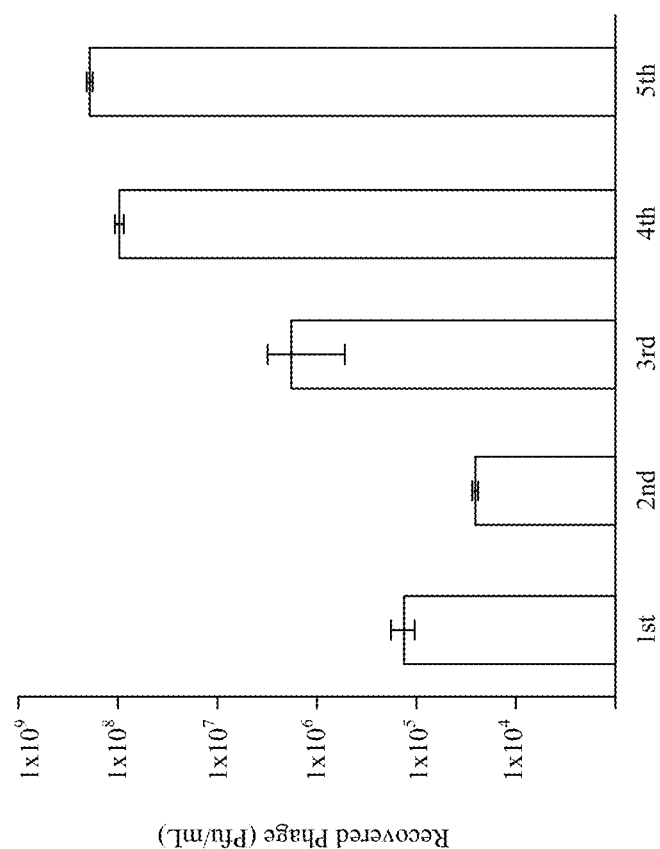
FIG. 1a is a bar graph depicting the number of recovered phages from each round of biopanning as detailed in Example 1, in accordance with aspects of the present disclosure.

Aspects herein are directed to polypeptides and compositions comprising the same. Additional aspects herein are directed to compositions comprising the peptides herein that may be utilized as a therapeutic agent for cancer treatment. In aspects, the polypeptides can exhibit blocking activity for the PD-1/PD-L1 interaction.

As discussed above, immunotherapy using checkpoint inhibitors, especially PD-1/PD-L1 inhibitors, has now evolved into the most promising therapy for cancer patients. However, most of these inhibitors are monoclonal antibodies, and their large size may limit their tumor penetration, leading to suboptimal efficacy. As a result, there has been a growing interest in developing low-molecular-weight checkpoint inhibitors. Compared to small molecules which often trigger side effects by toxic metabolites or nonspecific accumulation in the body, peptides can be metabolized to amino acids in the body and have a rare incidence of side effects. Further, peptides are much smaller than large proteins and antibodies. Low-molecular-weight peptides may provide mid-size therapeutic agents with high efficacy and low toxicity.

Furthermore, peptides may provide a better candidate than traditional small molecules for targeting protein/protein interactions. Compared to small molecules, peptides are bigger and therefore can cover a significant portion of the target interface. Peptides may be more efficient to block protein/protein interactions, such as the interactions between checkpoints and their receptors. Moreover, prediction of human doses of peptides through allometric scaling is more straightforward than that of small molecules. Compared to antibodies, low-molecular-weight peptides have several advantages, such as reduced immunogenicity, ease of manufacture, better tumor penetration, and lack of Fc-mediated side effects. However, there is a lack of low molecular weight peptides that can block the PD-1/PD-L1 interaction. Thus, there is a need for identifying and developing low molecular weight peptides for use as therapeutic agents for cancer treatment or other diseases.

The polypeptides and compositions disclosed herein alleviate one or more of the above-mentioned problems. For instance, the polypeptides disclosed herein are low molecular weight anti human PD-L1 peptides. In various aspects, one or more of the polypeptides disclosed herein can specifically bind to PD-L1 with high affinity and block the PD-1/PD-L1 interaction on tumor cells. In one or more aspects, one or more of the polypeptides disclosed herein exhibits better tumor penetration than that compared to anti-PD-L1 antibody. In certain aspects, one or more of the polypeptide disclosed herein can also inhibit tumor growth and/or can increase survival of CT26 tumor-bearing mice. In certain aspects, the one or more peptides disclosed herein can be low-molecular-weight inhibitors utilized for cancer immunotherapy. In aspects, the low-molecular-weight anti-PD-L1 peptides disclosed herein can be linked to a targeting ligand or encapsulated in a nanoscale delivery system to improve their accumulation in the tumor microenvironment, thus minimizing the non-specific blockade effect in other tissues expressing PD-L1.

Accordingly, in one aspect, a composition is provided. The composition includes a therapeutic agent. The therapeutic agent includes a polypeptide that comprises one or more amino acid sequences selected from the group consisting of: HYPFRPHANQAS (SEQ ID NO:1); WHRSYYTWNLNT (SEQ ID NO: 2); WHFSYN-WRWLPP (SEQ ID NO:3); DYHDPSLPTLRK (SEQ ID NO:4); CHRSYYTWNLNC, wherein a disulfide bond is present between the cysteine amino acids at positions 1 and 12 (SEQ ID NO:5); CHRSYYCWNLNT, wherein a disulfide bond is present between the cysteine amino acids at positions 1 and 7 (SEQ ID NO:6); and WHRSYYTWN (SEQ ID NO:7).

In another aspect, a composition is provided. The composition includes a polypeptide. The polypeptide exhibits at least 80% sequence identity to one or more amino acid sequences selected from the group consisting of: HYPFRPHANQAS (SEQ ID NO:1); WHRSYYTWNLNT (SEQ ID NO: 2); WHFSYNWRWLPP (SEQ ID NO:3); DYHDPSLPTLRK (SEQ ID NO:4); CHRSYYTWNLNC, wherein a disulfide bond is present between the cysteine amino acids at positions 1 and 12 (SEQ ID NO:5); CHRSYYCWNLNT, wherein a disulfide bond is present between the cysteine amino acids at positions 1 and 7 (SEQ ID NO:6); and WHRSYYTWN (SEQ ID NO:7).

In yet another aspect, a method of treating cancer in a mammalian subject in need of treatment is provided. The method includes administering to a subject a therapeutically effective amount of a therapeutic agent. The therapeutic agent comprising a polypeptide that comprises one or more amino acid sequences selected from the group consisting of: HYPFRPHANQAS (SEQ ID NO:1); WHRSYYTWNLNT (SEQ ID NO: 2); WHFSYNWRWLPP (SEQ ID NO:3); DYHDPSLPTLRK (SEQ ID NO:4); CHRSYYTWNLNC, wherein a disulfide bond is present between the cysteine amino acids at positions 1 and 12 (SEQ ID NO:5); CHRSYYCWNLNT, wherein a disulfide bond is present between the cysteine amino acids at positions 1 and 7 (SEQ ID NO:6); and WHRSYYTWN (SEQ ID NO:7).

Throughout this disclosure, the terms "peptide" and "polypeptide" are used interchangeably. Thus, unless specifically noted otherwise, "peptide" and "polypeptide" shall not limit one or the other, but shall be construed to have the same, broadest meaning.

Certain abbreviations may be utilized herein. A listing of their meaning is provided in this paragraph. 3D: three-dimensional; BSA: bovine serum albumin; CAR: chimeric antigen receptor; ECD: extracellular domain; ECM: extracellular matrix; ELISA: enzyme-linked immunosorbent assay; FBS: fetal bovine serum; FDA: Food and Drug Administration; IC50: half maximal inhibitory concentration; IHC: immunohistochemistry; irAEs: immune-related adverse events; KD or $K_D$: the equilibrium dissociation constant; MDSCs: myeloid-derived suppressor cells; PD-1: programmed cell death protein 1; PD-L1: Programmed death-ligand 1; and SPR: Surface Plasmon Resonance.

As discussed above, in aspects, one or more polypeptides are disclosed. In certain aspects, the one or more polypeptides can comprise one or more of the following: HYPFRPHANQAS (SEQ ID NO:1); WHRSYYTWNLNT (SEQ ID NO: 2); WHFSYNWRWLPP (SEQ ID NO:3); DYHDPSLPTLRK (SEQ ID NO:4); CHRSYYTWNLNC, wherein a disulfide bond is present between the cysteine amino acids at positions 1 and 12 (SEQ ID NO:5); CHRSYYCWNLNT, wherein a disulfide bond is present between the cysteine amino acids at positions 1 and 7 (SEQ ID NO:6); WHRSYYTWN (SEQ ID NO:7), or an amino acid sequence having at least 80% sequence identity to at least one of SEQ ID NOs:1-7.

In aspects, the one or more polypeptides can consist essentially of, or consist of, one or more of the following: HYPFRPHANQAS (SEQ ID NO:1); WHRSYYTWNLNT (SEQ ID NO: 2); WHFSYNWRWLPP (SEQ ID NO:3); DYHDPSLPTLRK (SEQ ID NO:4); CHRSYYTWNLNC, wherein a disulfide bond is present between the cysteine amino acids at positions 1 and 12 (SEQ ID NO:5); CHRSYYCWNLNT, wherein a disulfide bond is present between the cysteine amino acids at positions 1 and 7 (SEQ ID NO:6); WHRSYYTWN (SEQ ID NO:7), or an amino acid sequence having at least 80% sequence identity to at least one of SEQ ID NOs:1-7.

In aspects, the one or more polypeptides can include one or more copies of any of the amino acid sequences disclosed herein. In aspects, the one or more polypeptides can include one copy of any of the amino acid sequences disclosed herein, e.g., one copy of any of SEQ ID NOs: 1, 2, 3, 4, 5, 6, and/or 7. In various aspects, the one or more polypeptides can include two or more copies of any of the amino acid sequences disclosed herein, e.g., two or more copies of any of SEQ ID NOs: 1, 2, 3, 4, 5, 6, and/or 7. In such aspects, the one or more polypeptides can include additional amino acid(s) to space apart the sequences, which can be chosen by one skilled in the art for a particular purpose. In certain aspects, the two or more copies of any of the amino acid sequences disclosed herein (SEQ ID NOs:1-7) refers to a single polypeptide having at least: two copies of the same amino acid sequence (e.g., a single polypeptide having two or more copies of SEQ ID NO:7); and/or multiple of the amino acid sequences disclosed herein (e.g., a single polypeptide having one or more copies of SEQ ID NO:7 and one or more copies of SEQ ID NO: 2).

In various aspects, the one or more polypeptides comprise an amino acid sequence having at least 80%, at least 90%, at least 95%, or at least 99% sequence identity to one or more of SEQ ID NOs: 1, 2, 3, 4, 5, 6, and/or 7. In certain aspects, the one or more polypeptides consist essentially of an amino acid sequence having at least 80%, at least 90%, at least 95%, or at least 99% sequence identity to one or more of SEQ ID NOs: 1, 2, 3, 4, 5, 6, and/or 7. In aspects, the one or more polypeptides consist of an amino acid sequence having at least 80%, at least 90%, at least 95%, or at least 99% sequence identity to one or more of SEQ ID NOs: 1, 2, 3, 4, 5, 6, and/or 7.

In various aspects to arrive at a polypeptide with less than 100% sequence identity to at least one of SEQ ID NOs: 1, 2, 3, 4, 5, 6, and/or 7, any of the amino acids may be substituted on the basis of similarity in polarity, charge, solubility, hydrophobicity, hydrophilicity, and/or the amphipathic nature of the residues involved. For example: nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. In certain aspects, amino acid substitutions may be made on the basis of the hydropathic index of amino acids. In such aspects, each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The use of the hydropathic amino acid index in conferring interactive biological function on a protein is understood by one of skill in the art (Kyte and Doolittle, J. Mol. Biol. 157:105-132, 1982). It is known that in certain instances, certain amino acids may be substituted for other amino acids having a similar hydropathic index or score and still retain a similar biological activity. In making changes based upon the hydropathic index, in certain aspects the substitution of amino acids whose hydropathic indices are within ±2 is included, while in other, aspects amino acid substitutions that are within ±1 are included, and in yet other aspects amino acid substitutions within ±0.5 are included. It should be understood that the optional use of hydropathic index to make amino acid substitutions in any of the polypeptides disclosed herein is but one example for identifying and making amino acid substitutions to the one or more polypeptides disclosed herein and that other strategies known by one of skill in the art may also or alternatively be used.

In aspects, the one or more polypeptides disclosed herein can comprise L-amino acids, D-amino acids, or a combination thereof. In certain aspects, the one or more polypeptides can consist of L-amino acids. In alternative aspects, the one or more polypeptides can consist of D-amino acids.

In various aspects, as discussed above, the one or more polypeptides exhibits blocking activity to the PD-1/PD-L1 interaction. For instance, in certain aspects, the one or more polypeptides disclosed herein can bind to PD-L1 with high affinity and block the PD-1/PD-L1 interaction on tumor cells.

In certain aspects, the one or more polypeptides exhibits an equilibrium dissociation constant $K_D$ value against recombinant human PD-L1 that is less than about 600 nM (nanomolar), less than about 550 nM, less than about 400 nM, or less than about 300 nM; or of from about 0.1 nM to about 600 nM, of from about 0.1 nM to about 550 nM, or of from about 0.1 nM to about 300 nM. In such aspects, the equilibrium dissociate constant $K_D$ value against recombinant human PD-L1 can be determined according to an $K_D$ to PD-L1 SPR Assay. The $K_D$ to PD-L1 SPR Assay can include the use of Surface Plasmon Resonance (SPR), such as the BI4500, Biosensing Instrument, and can include the following procedures. The PD-L1 protein can be diluted to 10 μg/mL with sodium acetate buffer (pH 5.0, GE Healthcare, PA) and covalently coated onto a CM5 sensor chip (CM Dextran Sensor Chip, Biosensing Instrument) using the standard Amine Coupling Kit (GE Healthcare, PA). Approximately 6500 RU of PD-L1 protein are immobilized onto the chip. A second channel is used as a reference. HBS-EP+ buffer (GE Healthcare) can be employed at a flow rate of 60 μL/min. A series of concentrations of each peptide (15, 30, 60, 125, 250, 500, 1000, 5000 and 10,000 nM) is prepared in HBS-EP+ running buffer to obtain the equilibrium dissociation constant ($K_D$) values of the peptides. The CM5 sensor chip can be regenerated with 10 mM NaOH for 20 s. The results can be analyzed using the software of Bi data analysis software.

As discussed above, various aspects can include compositions that include a therapeutic agent, wherein the therapeutic agent includes one or more of the peptides disclosed herein. In certain aspects, the therapeutic agent can be a therapeutic agent for treating one or more cancers. In one aspect, the therapeutic agent can be a therapeutic agent for treating one or more cancerous tumors. In aspects, the method can include administering a therapeutically effective amount of the compositions and/or peptides disclosed herein to a mammalian subject. In various aspects, a therapeutically effective amount of the one or more compositions and/or peptides disclosed herein refers to an amount that will lessen or alleviate one or more symptoms of the disease or condition, or causes of the disease or condition that is being treated.

In aspects, the compositions disclosed herein can be used in a method for treating cancer in a mammalian subject in need of treatment. In aspects, the mammalian subject can be a human. In such aspects, the compositions can be administered to the mammalian subject using any technique known in the art. For instance, in aspects, the compositions can be administered using any of the following non-limiting example methods: subcutaneous, intravenous, intraperitoneal, orally, and/or parenternaly.

In aspects, a pharmaceutically acceptable carrier or formulation material may be added to the compositions and/or polypeptides prior to or during administration. Example pharmaceutically acceptable carriers or formulation materials are described below.

Formulation materials and pharmaceutically acceptable carriers may be used for modifying, maintaining, or preserving, for example, the pH, osmolarity, viscosity, clarity, color, isotonicity, odor, sterility, stability, rate of dissolution or release, adsorption or penetration of one or more of the compositions or polypeptides discussed above. Suitable materials include, but are not limited to amino acids (for example, glycine, glutamine, asparagine, arginine and lysine); antimicrobials; antioxidants (for example, ascorbic acid, sodium sulfite and sodium hydrogen-sulfite); buffers (for example, borate, bicarbonate, Tris-HCl, citrates, phosphates and other organic acids); bulking agents (for example, mannitol and glycine); chelating agents (for example, ethylenediaminetetraacetic acid (EDTA)); complexing agents (for example, caffeine, polyvinylpyrrolidone, beta-cyclodextrin, and hydroxypropyl-beta-cyclodextrin); fillers; monosaccharides, disaccharides, and other carbohydrates (for example, glucose, mannose and dextrins); proteins (for example, serum albumin, gelatin and immunoglobulins); coloring, flavoring, and diluting agents; emulsifying agents; hydrophilic polymers (for example, polyvinylpyrrolidone); low molecular weight peptides; salt-forming counterions (for example, sodium); preservatives (for example, benzalkonium chloride, benzoic acid, salicylic acid, thimerosal, phenethyl alcohol, methylparaben, propylparaben, chlorhexidine, sorbic acid and hydrogen peroxide); solvents (for example, glycerin, propylene glycol and polyethylene glycol); sugar alcohols (for example, mannitol and sorbitol); suspending agents; surfactants or wetting agents (for example, pluronics, PEG, sorbitan esters, polysorbates (for example, polysorbate 20 and polysorbate 80), triton, tromethamine, lecithin, cholesterol, and tyloxapal); stability enhancing agents (for example, sucrose and sorbitol); tonicity enhancing agents (for example, alkali metal halides (for example, sodium or potassium chloride), mannitol, and sorbitol); delivery vehicles; diluents; excipients; and pharmaceutical adjuvants ("Remington's Pharmaceutical Sciences", 18'h Ed. (Gennaro, ed., Mack Publishing Company, Easton, Pa., 1990)).

The present disclosure can be further illustrated by the following examples of aspects thereof, although it will be understood that these examples are included merely for purposes of illustration and are not intended to limit the scope of the disclosure unless otherwise specifically indicated.

EXAMPLES

Methods

Cell Culture. MDA-MB231, DU-145, CT26, 4T1 and Jurkat cells were purchased from ATCC. MDA-MB231 and DU-145 cells were cultured in DMEM medium with 10% Fetal Bovine Serum (FBS), 100 units/mL penicillin and 100 μg/mL streptomycin. CT26, 4T1, and Jurkat cells were cultured in RPM11640 medium with 10% FBS, 100 units/mL penicillin and 100 μg/mL streptomycin. All cells were grown at 37° C. in a humidified atmosphere containing 5% $CO_2$.

Biopanninq Procedure. A novel biopanning procedure was developed to discover peptides that specifically bind to PD-L1. Briefly, the recombinant human PD-L1 extracellular domain (ECD) protein (cat #FCL0784B, G&P Biosciences, Santa Clara, Calif.) was coated on two wells of a 96-well plate. On the first well, PD-L1 was incubated with PD-1 protein, followed by incubation with the Ph.D.™-12 Phage Display Peptide Library (NEB, Ipswich, Mass.). The unbound phages were transferred to the second well, which coated with PD-L1. The unbound phages were then washed away, and the bounded phages were eluted and amplified. In each biopanning, approximately $10^{11}$ pfu phages were loaded, and eluted phages were tittered and amplified for the next round of selection.

Blockade of the PD-1/PD-L1 Interaction. Ninety-six-well plates were coated with 100 ng of PD-L1 protein (G&P Biosciences, human PD-L1 ECD, cat #FCL0784B. mouse PD-L1, cat #FCL3502B) and later blocked with 2% BSA for 2 hours at room temperature. Various concentrations of peptides were loaded into the wells and incubated for 1 hour at room temperature. Biotinylated PD-1 (G&P Biosciences, human PD-1 ECD, cat #FCL0761B; mouse PD-1, cat #FCL1846) was added and incubated for 1 hour. Streptavidin-HRP (R & D systems) and chromogenic substrate were added into the wells. $OD_{450}$ was then recorded and referenced to $OD_{540}$.

Evaluation of Binding Kinetics and Affinity By Surface Plasmon Resonance (SPR). Binding affinities of the PD-L1 specific peptides for human PD-L1 protein were determined by SPR (B14500, Biosensing Instrument). PD-L1 protein was diluted to 10 μg/mL with sodium acetate buffer (pH 5.0, GE Healthcare, PA) and covalently coated onto a CM5 sensor chip (CM Dextran Sensor Chip, Biosensing Instrument) using the standard Amine Coupling Kit (GE Healthcare, PA). Approximately 6500 RU of PD-L1 protein were immobilized onto the chip. A second channel was used as a reference. HBS-EP+ buffer (GE Healthcare) was employed at a flow rate of 60 μL/min. A series of concentrations of each peptide (15, 30, 60, 125, 250, 500, 1000, 5000 and 10,000 nM) were prepared in HBS-EP+ running buffer to obtain the equilibrium dissociation constant ($K_D$) values of the peptides. The CM5 sensor chip was regenerated with 10 mM NaOH for 20 seconds. The results were analyzed using the software of Bi data analysis software. Binding affinities of the anti-PD-L1 peptides to BSA was also assessed following the procedure for human PD-L1.

Binding Specificity of the Anti-PD-L1 Peptides Towards PD-L1 Overexpressing Cancer Cells. Binding of the peptides to PD-L1-positive cancer cells (MDA-MB-231 and DU-145) and PD-L1-negative cancer cells (MCF-7) was evaluated as previously described with modifications (Chen, Z. et al. Discovery of Aptamer Ligands for Hepatic Stellate Cells Using SELEX. Theranostics 7, 2982-2995 (2017)). The cells were treated with the non-enzymatic cell dissociation solution (MP Biomedicals, Santa Ana, CA) and diluted to a density of $1 \times 10^6$ cells/mL in Opti-MEM. The suspended cells were incubated with various concentrations of 5-FAM-labeled anti-PD-L1 peptides or Cy5-labeled PD-L1 antibody for 1 hour at 37° C. with gentle rotation. After washing, the cells were analyzed using a FACSCalibur flow cytometer (BD Biosciences, Franklin Lakes, N.J.).

3D Tumor Spheroid Penetration Assay. 3D spheroids of MDA-MB-231 cells were generated using the Spheroid Formation Extracellular Matrix (ECM) as per the company's protocol (Amsbio, Cambridge, MA). Briefly, 3,000 tumor cells were mixed with 50 μL Spheroid Formation ECM and loaded into a Corning™ 96-well Ultra-low Attachment Treated Spheroid Microplate (Corning, Pittsburgh, PA). The plate was centrifuged at 200 g for 3 min at 4° C. The cells were then incubated at 37° C. until the diameter reached approximately 700 μm. The Cy5-labeled CLP002 peptide and anti-PD-L1 antibody were incubated with the spheroids for 2 or 6 hours. After washing, penetration of the peptide and antibody inside the tumor spheroids was determined using confocal microscopy.

Proliferation and Apoptosis Assays. Proliferation and apoptosis of Jurkat T cells were assessed as described (Freeman, G. J. et al. Engagement of the PD-1 immunoinhibitory receptor by a novel B7 family member leads to negative regulation of lymphocyte activation. *The Journal of experimental medicine* 192, 1027-1034 (2000); Dong, H. et al. Tumor-associated B7-H1 promotes T-cell apoptosis: a potential mechanism of immune evasion. Nature medicine 8, 793-800 (2002)). Briefly, $3 \times 10^4$ Jurkat T cells were cultured alone or co-cultured with $1.5 \times 10^5$ DU-145 cancer cells in a 24-well plate for the proliferation assay. For the apoptosis assay, $6 \times 10^4$ Jurkat T cells were cultured alone or co-cultured with $3 \times 10^5$ DU-145 cancer cells in a 6-well plate. After incubation with the anti-PD-L1 peptides (5 μM) or anti-PD-L1 antibody (1 μM) for 24 hours, Jurkat T cells were harvested from the supernatant. Proliferation of Jurkat cells was determined using the CellTiter-Glo luminescent cell viability assay (Promega, WI), and apoptosis of the cells were determined using the Dead Cell Apoptosis Kit with Annexin V Alexa Fluor® 488 and Propidium Iodide (Thermo-Fisher Scientific, Pittsburgh, PA) as we described before[21].

Molecular Docking of the Binding of the Anti-PD-L1 Peptides. The crystal structure of human PD-L1 protein (PDB ID: 5C3T) and its binding residues to PD-1 were reported previously (Zak, K. M. et al. Structure of the Complex of Human Programmed Death 1, PD-1, and Its Ligand PD-L1. Structure 23, 2341-2348 (2015)). Structures of the peptides were generated using BIOVIA Draw (BIOVIA) and then aligned to the PD-L1 structure using Autodock Vina. Illustrations of the PD-L1 protein and peptide complex were generated using Pymol (Delano Scientific).

Animal Study. The animal protocol was approved by the University of Missouri-Kansas City, Institutional Animal Care and Use Committee (IACUC). Five-week old male and female Balb/c mice were purchased from Charles Rivers Laboratories (Wilmington, Mass.) and housed in a temperature and humidity controlled room on a 12-hour light-dark cycle. Approximately $5 \times 10^5$ CT26 cells were subcutaneously injected into the right flank. The mice were randomly divided into five different groups (10 mice/group, 50% female, 50% male). The mice were intraperitoneally injected with 2 mg/kg peptide daily when the tumor size reached 50-100 mm$^3$. The anti-mouse PD-L1 antibody (10F.9G2, BioXcell) was administered as a positive control at a dose of 10 mg/kg every two days. The tumor size was assessed with a caliper and calculated with the formula $0.5 \times length \times width^2$. ELISA kits of PD-L1 (Cat #DY1019-05), IFNγ (Cat #DY485-05), and IL-6 (Cat #DY406-05) were used to measure the expressions of PD-L1, IFNγ, and IL-6, respectively, in tumors as per the company's instructions (R & D Systems, Minneapolis, MN).

Immunohistochemistry (IHC) Staining. Tumor tissues were fixed in 10% formalin, embedded in paraffin, sectioned, and mounted on glass slides by Truman Medical Centers Anatomic Pathology Core (Kansas City, MO). The slides were heated in Tris buffer (pH 9.0) for 45 min to recover antigen. After deparaffinization and rehydration, the sections were stained with the anti-mouse CD8 alpha antibody (Abcam, ab209775) overnight at 4° C. The slides were incubated with a biotinylated goat anti-rabbit secondary antibody, followed by the DAB chromogen mixture. Four sections (2 male and 2 female) were imaged in each group. For each section, 3 regions were randomly selected for imaging.

Statistical Analysis. Data are expressed as the mean±standard deviation (SD). The difference between any two groups was determined by one-way analysis of variance (ANOVA) with Tukey's post hoc test. The difference between any two groups was determined by two-way ANOVA with Tukey's post hoc test. $P < 0.05$ was considered statistically significant.

Blocking efficiency at 10 μM/$IC_{50}$ against human and mouse PD1/PD-L1 (ELISA). Human PD-1 (Biotinylated): PD-L1 inhibitor screening ELISA assay pair (Acro Biosystems, cat #EP-101) was used in the blocking assay and IC50 determination. 100 ng of recombinant human PD-L1 protein was coated in 96-well plates at 4° C. for 16 h with shaking over an orbital shaker. Unbound protein was removed by washing twice with PBS (pH 7.2-7.4), 2% BSA was added for 1.5 h at 37° C. to block the plate. Specific concentrations of the peptides were dispensed into the appropriate wells and incubated for 2 h at 37° C. Biotinylated PD-1 was subsequently added and incubated for 1.5 h. This was followed by the addition of streptavidin-HRP and chromogenic substrate (R & D systems). The color reaction was terminated with 2N $H_2SO_4$, absorbance was recorded at OD450 and referenced to OD540. PD-L1 blocking activity of the peptides was also assessed using mouse PD-1 (Biotinylated, Acro Biosystems, cat #PD1-M82F4) and PD-L1 (Acro Biosystems, cat #PD1-M5220) following the same procedure as for the human proteins.

Example 1: Discovery of Anti-PD-L1 Peptides Using Biopanning and Binding Affinity and Specificity of the Peptides to PD-L1

In this Example, small peptides were identified that not only specifically bind to PD-L1 but also block the interaction between PD-L1 and PD-1. In this Example, a novel biopanning strategy to select peptides that specifically bind to PD-L1 was utilized as described above. As FIG. 1a shows, after five rounds of biopanning, the number of eluted phages increased dramatically, indicating significant enrichment of PD-L1-specific phages in the elution. Totally 57 single phage colonies were randomly selected for sequencing, and 4 peptide sequences were discovered (see Table 1 below). The CLP002 peptide (SEQ ID NO:2) and CLP003 peptide (SEQ ID NO:3) have 21 and 32 repeats, respectively, while the CLP001 peptide and CLP004 peptide have 1 and 3 repeats, respectively, in the biopanning results.

TABLE 1

Biopanning Results

| Peptides | Sequences | Frequency | $K_a$ $(M^{-1}S^{-1})$ | $K_d$ $(S^{-1})$ | $K_D$ (nM) |
|---|---|---|---|---|---|
| CLP001 - (SEQ ID NO: 1) | HYPFRPHANQAS | 1 | 5186 +/- 212 | (2.81 +/- 0.50) × $10^3$ | 534 +/- 54 |
| CLP002 - (SEQ ID NO: 2) | WHRSYYTWNLNT | 21 | 4521 +/- 666 | (1.45 +/- 0.92) × $10^3$ | 366 +/- 150 |
| CLP003 - (SEQ ID NO: 3) | WHFSYNWRWLPP | 32 | (2.26 +/- 2.03) × $10^4$ | (1.62 +/- 0.11) × $10^3$ | 117 +/- 80 |
| CLP004 - (SEQ ID NO: 4) | DYHDPSLPTLRK | 3 | 5140 +/- 390 | (2.75 +/- 0.20) × $10^3$ | 544 +/- 81 |

% Blocking efficiency at 10 µM (Competitive SPR)/IC50 (competitive SPR) hPD-L1. BI-4500A SPR and a CM-5 sensor chip pre-functionalized with streptavidin (Biosensing Instrument Inc., Tempe, Ariz.) were employed for the SPR analysis. Biotinylated PD-1 (BPS Bioscience, cat #71109) was immobilized on the sensor chip to give coating of approximately 750 Response Units. Different concentrations of each peptide were incubated with human PD-L1 (Acro-Biosystems, cat #EP-101) prior to injection. Human PD-L1 alone was also injected to serve as a control. The ability of the peptides to block the binding interaction between PD-L1 and PD-1 was assessed by the change in response observed between the control and peptide samples. Data was analyzed with SPR Data Analysis Version 3.8.4 (Biosensing Instrument Inc., Tempe, AZ).

Half-life in 50% human serum. Proteolytic stability of the peptides was investigated using LC-MS. Solutions of the anti-PD-L1 peptides were incubated with 50% human serum at 370° C., aliquots were taken at specific time points for processing and subsequent LC-MS analysis.

% cell viability after incubation with 50 µM peptide. White 96-well plates with clear bottom (Corning, RFE 3610) were seeded with DU145 cells at a density of 1×$10^4$ cells/well and incubated in a humidified atmosphere at 37° C. with a supply of 5% $CO_2$. After 12 h, various peptide concentrations were added to the cells and incubated for 48 h. CellTiter-Glo kit (Promega, WI) was employed in the cell viability analysis by following the manufacturer's instructions.

Figure 1B:
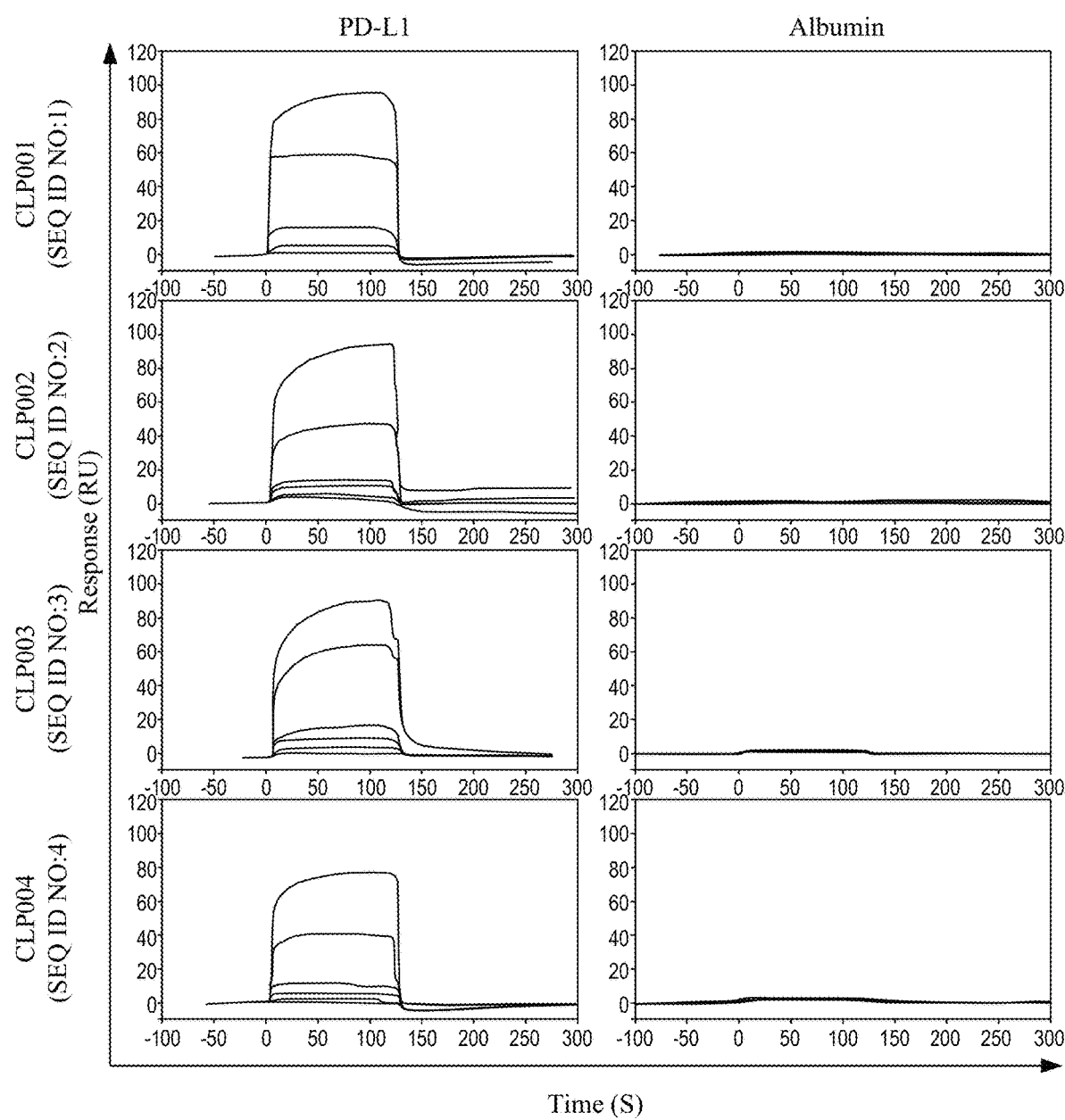
FIG. 1b is a series of graphs depicting the SPR sensograms of the peptides to immobilized human PD-L1 protein and BSA as detailed in Example 1, in accordance with aspects of the present disclosure.

Binding affinities of the discovered peptides against the recombinant human PD-L1 ECD protein were evaluated using SPR. The PD-L1 protein was immobilized on a CM5 golden chip by the direct amine coupling method. As illustrated in FIGS. 1b and 1n Table 1, the $K_D$ values of CLP001 (SEQ ID NO1), CLP002 (SEQ ID NO:2), CLP003 (SEQ ID NO:3), and CLP004 (SEQ ID NO:4) for human PD-L1 were 534, 366, 117, and 544 nM (nanomolar), respectively. The peptides can be considered competitive against the PD-1/PD-L1 interaction measured to have a $K_D$=~4 µM (micromolar). Even though the binding affinity of these peptides are generally lower than that of antibodies, the very high affinity of antibodies may result in on-target, off-tumor toxicity in healthy tissues that express low levels of PD-L1. In a recent study, scientists constructed several chimeric antigen receptor (CAR) T cells with different affinities to ICAM-1. CAR-T cells with micromolar affinity to ICAM-1 showed better antitumor efficacy and safety than CAR-T cells with nanomolar affinity. CAR-T cells with nanomolar affinity lyse healthy cells that express a low level of ICAM-1. By contrast, CAR-T cells with micromolar affinity only attack tumor cells with high levels of ICAM-1 but not healthy cells with low levels of ICAM-1, leading to less toxicity (Park, S. et al. Micromolar affinity CAR T cells to ICAM-1 achieves rapid tumor elimination while avoiding systemic toxicity. *Scientific reports* 7, 14366 (2017).

Figure 1C:
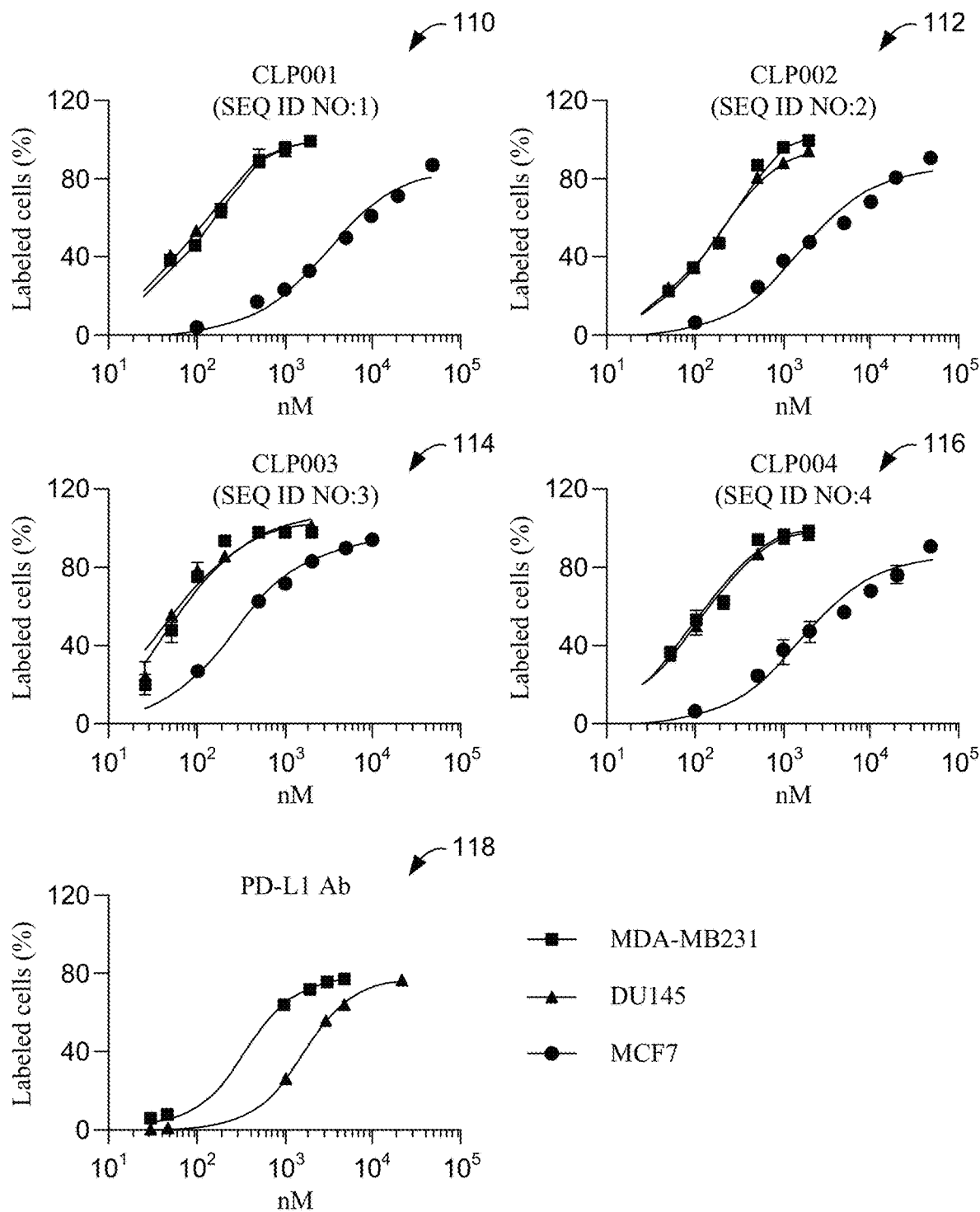
FIG. 1c is a series of graphs depicting binding curves of the peptides on PD-L1-positive human cancer cells (MDA-MB-231 and DU-145) and PD-L1 deficient human cancer cells MCF-7, and of the binding curves of anti-PD-L1 antibody were measured on DU-145 and MCF-7 cells as detailed in Example 1, in accordance with aspects of the present disclosure.

The specificity of these peptides was also evaluated. Nonspecific binding of the peptides against bovine serum albumin (BSA) using SPR was measured. As revealed in FIG. 1b, the response curves of BSA to the peptides did not change with gradient concentrations of the peptides, indicating negligible binding between the peptides and BSA. By contrast, the response curves of the peptides to the PD-L1 protein were correlated with the peptide concentrations. The peptides specificity to PD-L1-positive human cancer cells DU-145 was also tested. MCF-7 human cancer cells are PD-L1 deficient and used as a negative control in this study. As FIG. 1c shows, all peptides and PD-L1 antibody (29E.2A3, BioXcell, West Lebanon, NH) exhibited high binding affinity to PD-L1-positive cancer cells (DU-145) but low affinity to PD-L1-deficient human cancer cells MCF-7. Results are represented as the mean±SD (n=3). These results suggest that the anti-PD-L1 peptides specifically bind to recombinant human PD-L1 protein as well as PD-L1 overexpressing human cancer cells.

Example 2: Blockade of the PD-1/PD-L1 Interaction

Figure 2A:
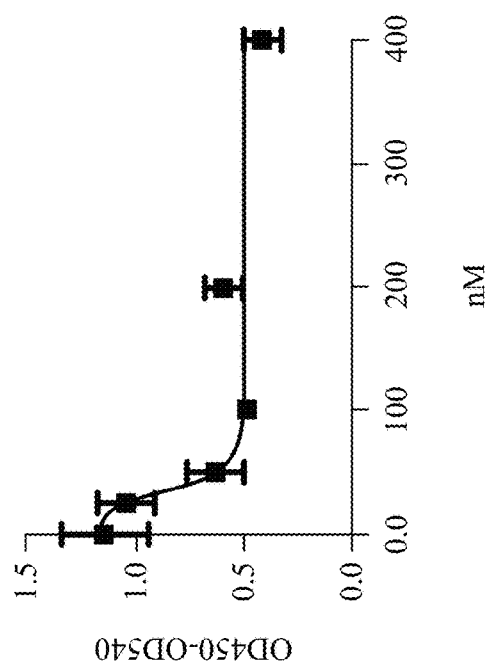
FIG. 2a is a graph depicting the blocking profile of the anti-human PD-L1 antibody (R & D, AF156) against human PD-L1 protein as detailed in Example 2, in accordance with aspects of the present disclosure.
Figure 2B:
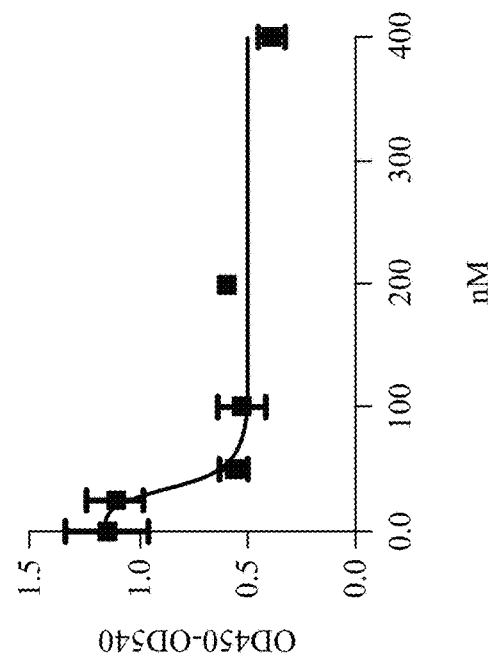
FIG. 2b is a graph depicting the blocking profile of an anti-human PD-L1 antibody against DU-145 cells as detailed in Example 2, in accordance with aspects of the present disclosure.
Figure 2C:
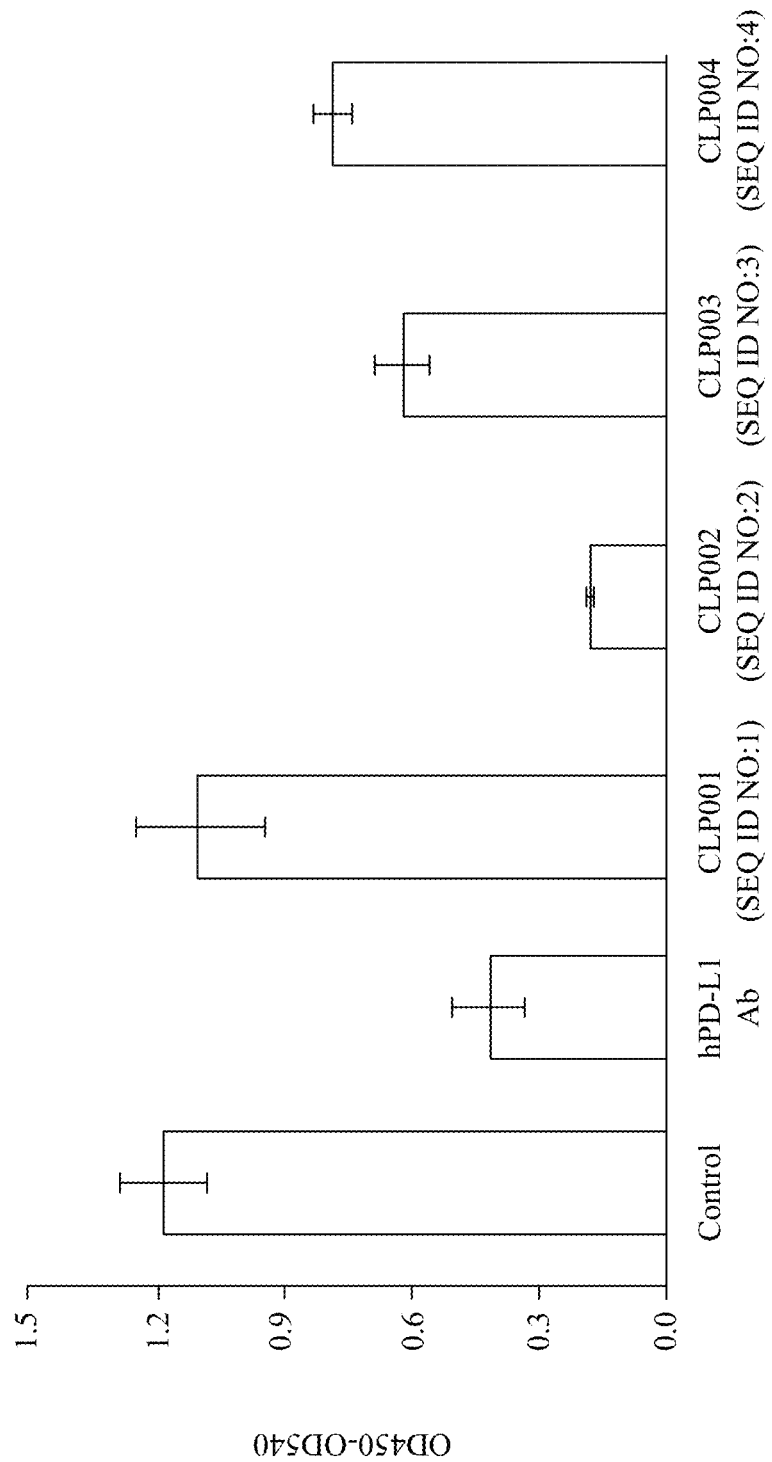
FIG. 2c is a graph depicting the blocking efficiency of certain anti-PD-L1 peptides (10 μM) and the anti-human PD-L1 antibody (1 μM) against human PD-L1 protein as detailed in Example 2, in accordance with aspects of the present disclosure.
Figure 2D:
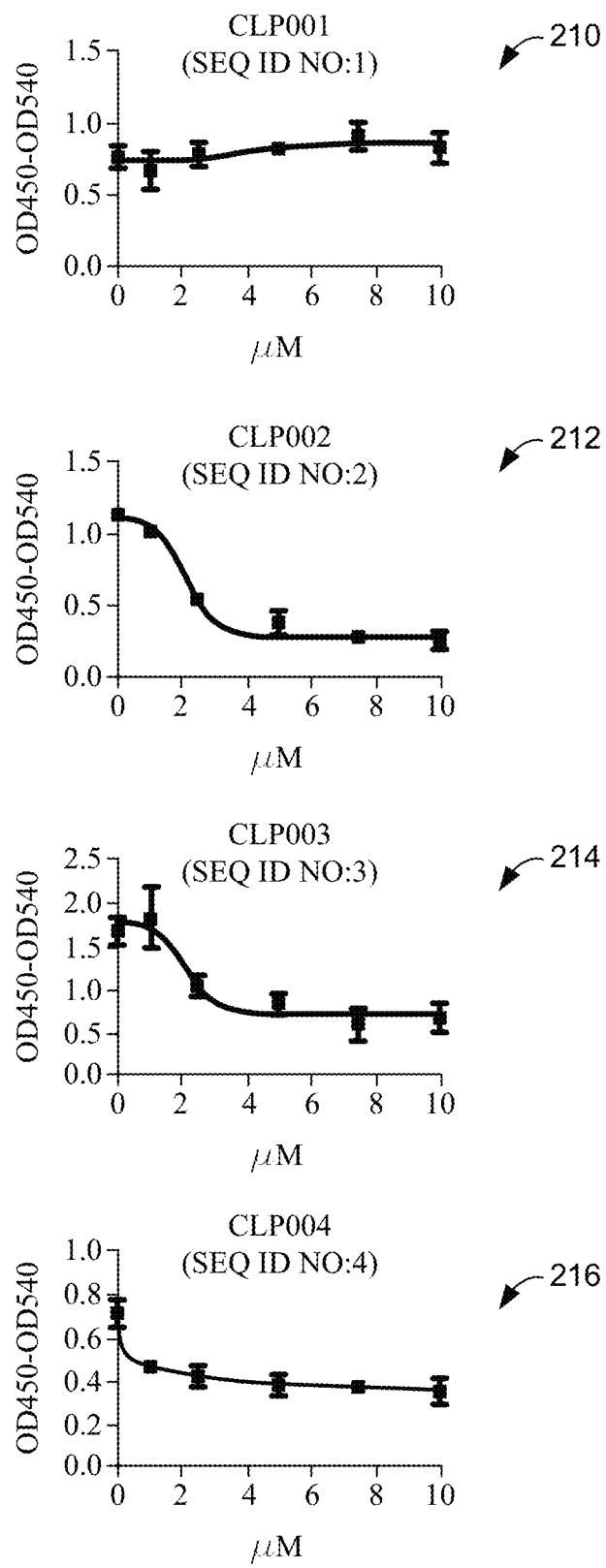
FIG. 2d is a series of graphs depicting the blocking profiles of certain peptides against human PD-L1 protein as detailed in Example 2, in accordance with aspects of the present disclosure.

It was next determined whether the anti-PD-L1 peptides block the human PD-1/PD-L1 interaction. An anti-human PD-L1 antibody (R & D Systems, cat #AF156) was used as a positive control to calibrate this assay. As shown in FIG. 2a, the anti-human PD-L1 antibody blocked the PD-1/PD-L1 interaction with a half-maximal inhibitory concentration ($IC_{50}$) of 36.76 nM, which is consistent with the report from the company. $IC_{50}$ of the antibody against PD-L1 overexpressing DU-145 cancer cells is 38.11 nM, which is comparable to the blocking effect on PD-L1 protein (FIG. 2b). The blocking efficiency of the anti-PD-L1 peptides at 10 μM (FIG. 2c). CLP002 (SEQ ID NO:2) showed the highest blocking efficiency, whereas CLP001 (SEQ ID NO:1) did not block the PD-1/PD-L1 interaction. The blocking efficiency of the anti-human PD-L1 antibody (1 μM) against the human PD-L1 protein was also determined. The $IC_{50}$ of each peptide was also determined using recombinant human PD-L1 protein and DU-145 cancer cells. As revealed in FIG. 2d, 2e, and Table 2 below, CLP002 (SEQ ID NO:2) exerted the best blocking effect (85%) with an $IC_{50}$ of 2.17 μM, when the plate was coated with the human PD-L1 protein. The blocking effect was 80% with an $IC_{50}$ of 1.43 μM, when the plate was coated with DU-145 cells. IC50 of the CLP003 (SEQ ID NO:3) peptide was 2.22 μM with 60% blocking efficiency against the human PD-L1 protein, and the IC50 was 3.05 μM with a 56% blocking efficiency against DU-145 cancer cells.

TABLE 2

IC50 and Blocking Efficiency

| Peptide | Target | $IC_{50}$ | Blocking Efficiency (%) |
| --- | --- | --- | --- |
| CLP001 - (SEQ ID NO: 1) | hPD-L1 protein | NA | 0 |
| | DU145 cancer cell | NA | 0 |
| CLP002 - (SEQ ID NO: 2) | hPD-L1 protein | 2.17 μM | 85 |
| | DU145 cancer cell | 1.43 μM | 80 |
| CLP003 - (SEQ ID NO: 3) | hPD-L1 protein | 2.22 μM | 60 |
| | DU145 cancer cell | 3.05 μM | 56 |
| CLP004 - (SEQ ID NO: 4) | hPD-L1 protein | 1.17 μM | 52 |
| | DU145 cancer cell | 0.20 μM | 60 |
| hPD-L1 Antibody | hPD-L1 protein | 36.76 nM | 63 |
| | DU145 cancer cell | 38.11 nM | 66 |

Figure 2E:
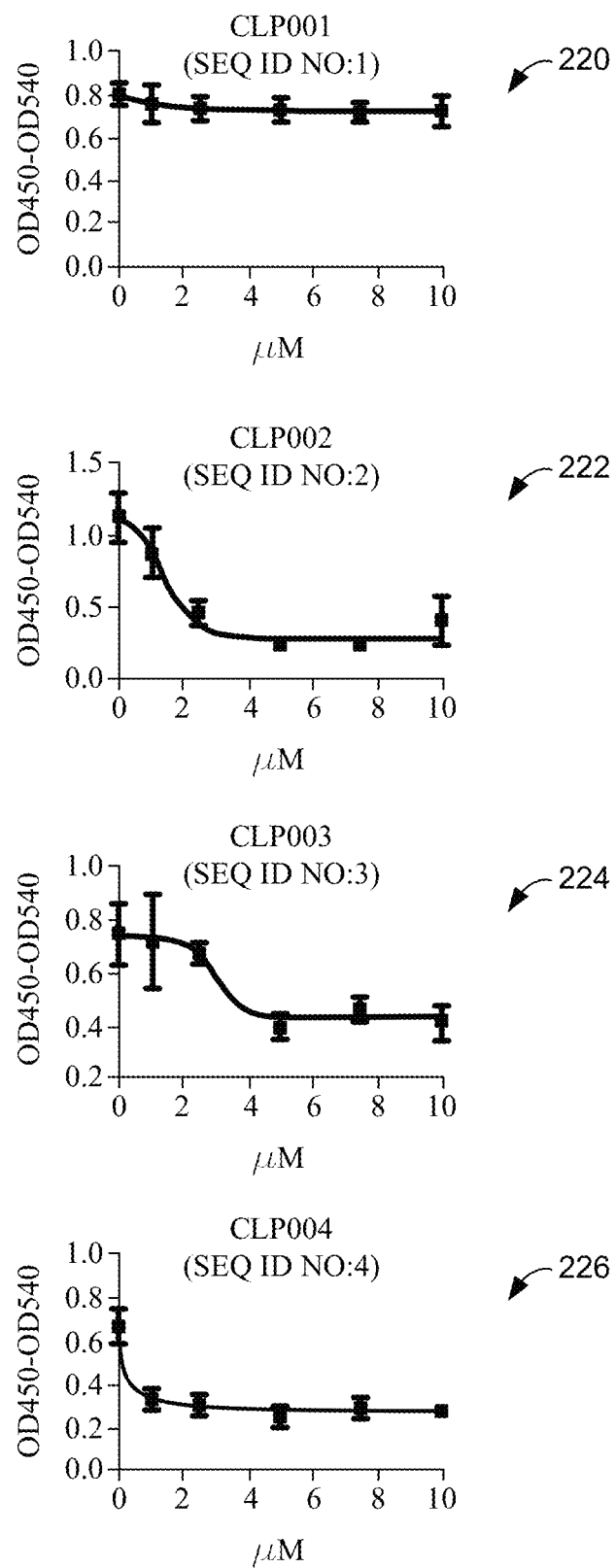
FIG. 2e is a series of graphs depicting the blocking profiles of certain peptides against DU-145 cells as detailed in Example 2, in accordance with aspects of the present disclosure.
Figure 2F:
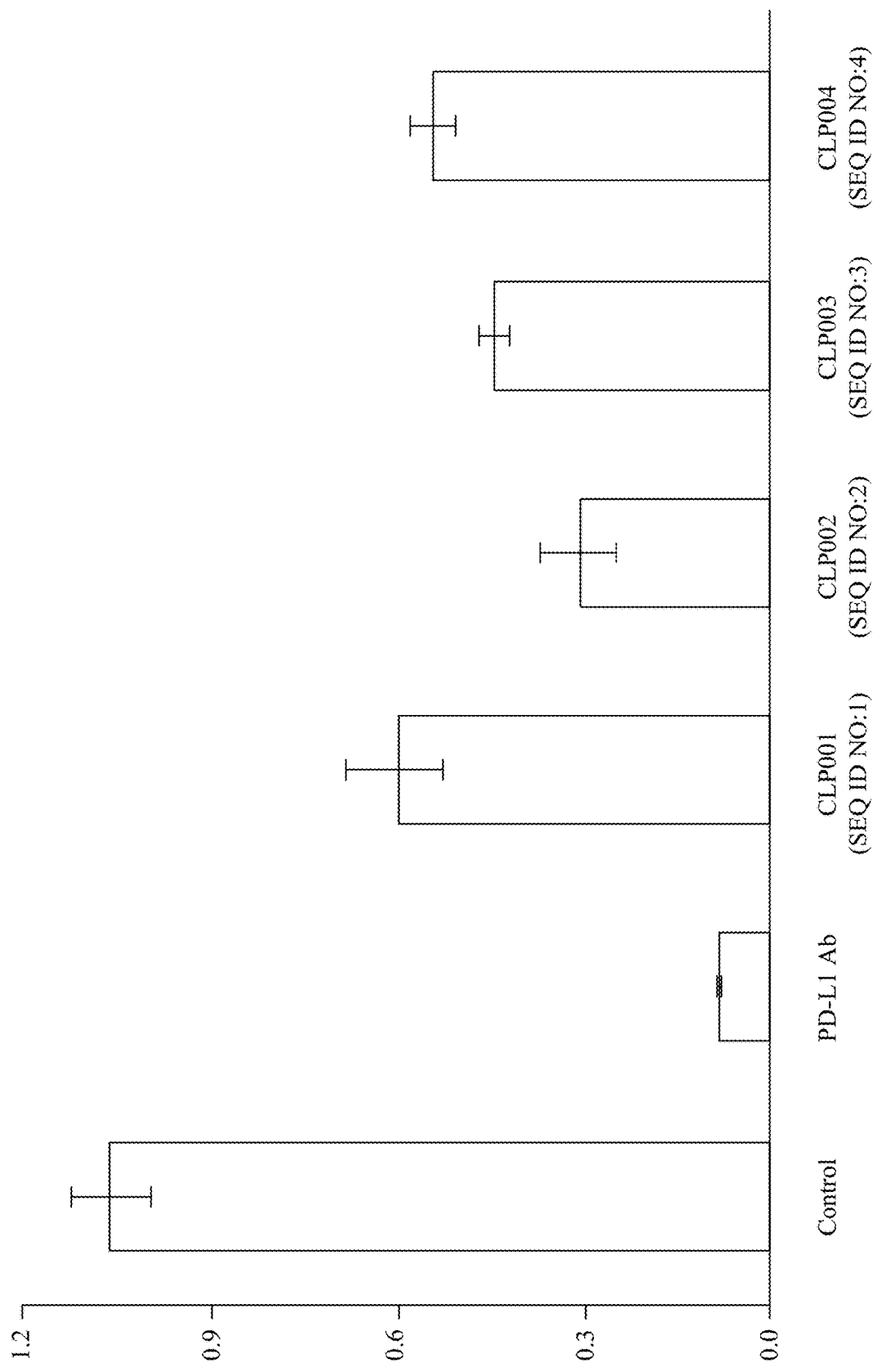
FIG. 2f is a graph depicting the blocking efficiency of the peptides and an anti-mouse PD-L1 antibody at 10 μM against a mouse PD-L1 protein as detailed in Example 2, in accordance with aspects of the present disclosure.
Figure 2G:
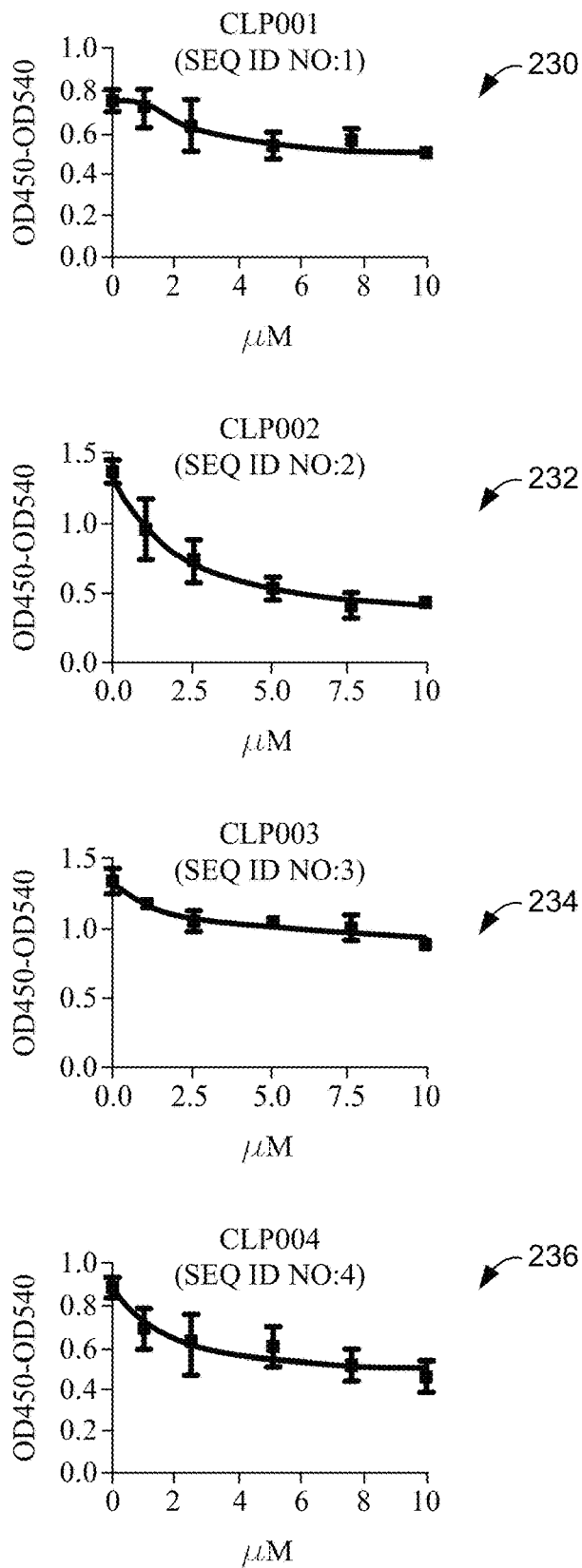
FIG. 2g is a series of graphs depicting the blocking profiles of certain peptides against mouse PD-L1 protein as detailed in Example 2, in accordance with aspects of the present disclosure.
Figure 2H:
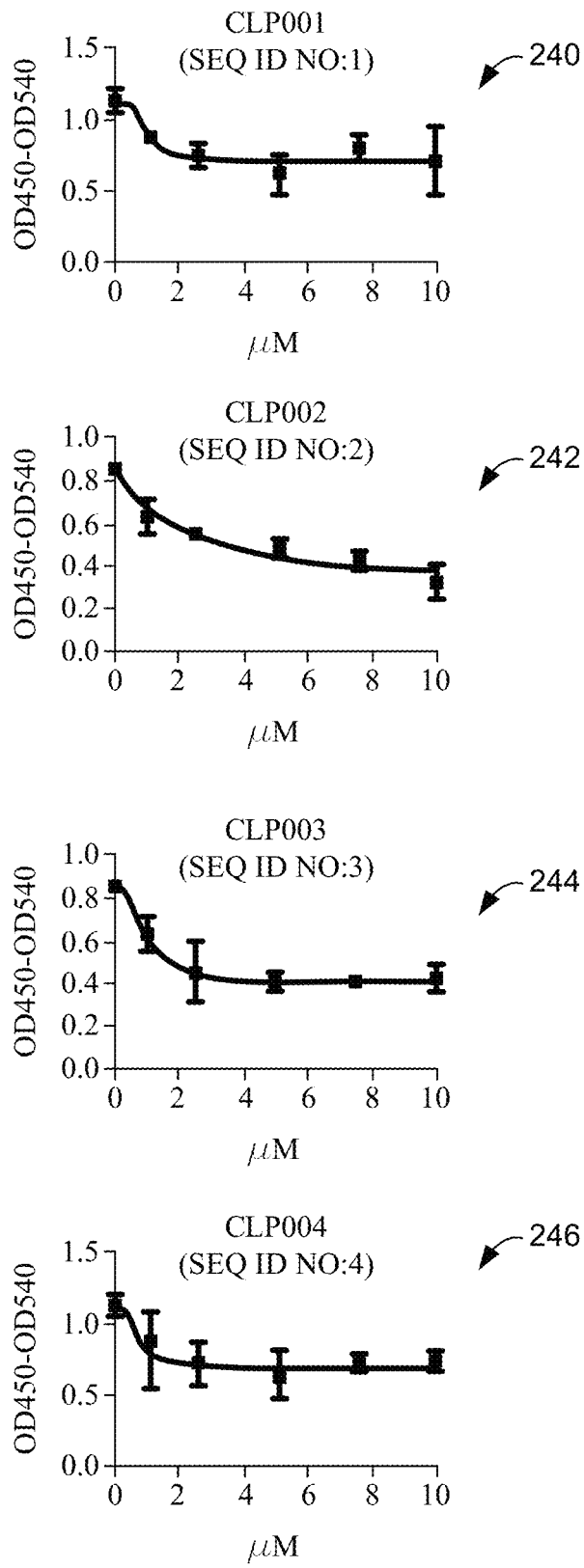
FIG. 2h is a series of graphs depicting the blocking profiles of certain peptides against mouse cancer cell line 4T1 as detailed in Example 2, in accordance with aspects of the present disclosure.

Blocking efficiencies of the peptides against mouse PD-1/PD-L1 interaction was also evaluated. As shown in FIG. 2f, blocking efficiencies of the peptides and an anti-mouse PD-L1 antibody (BioXcell, 10F.9G2) were compared at 10 μM. CLP002 (SEQ ID NO:2) blocked 71% of the mouse PD-1/PD-L1 interactions, while CLP003 (SEQ ID NO:3) blocked approximately 46% of the interactions. By contrast, the blocking efficiency of the anti-mouse PD-L1 antibody was 92%. This may be because CLP002 (SEQ ID NO:2) and CLP003 (SEQ ID NO:3) were discovered against human PD-L1 protein and therefore may have less binding affinity to mouse PD-L1 or less overlap with the mouse PD-1/PD-L1 interaction residues. $IC_{50}$ values of the peptides to block the mouse PD-1/PD-L1 interaction were also determined. As revealed in FIG. 2g, 2h, and Table 3 below, the $IC_{50}$ of CLP002 (SEQ ID NO:2) was 1.51 μM with a 71% blocking efficiency, while the $IC_{50}$ of CLP003 (SEQ ID NO:3) was 1.96 μM with a 46% blocking efficiency. In summary, the CLP002 (SEQ ID NO:2) peptide displayed the highest blocking efficiency against the PD-1/PD-L1 interaction.

TABLE 3

$IC_{50}$ and Blocking Efficiency

| Peptide | Target | $IC_{50}$ | Blocking Efficiency (%) |
| --- | --- | --- | --- |
| CLP001 - (SEQ ID NO: 1) | mPD-L1 protein | 2.43 μM | 34 |
| | 4T1 cancer cell | 0.91 μM | 35 |
| CLP002 - (SEQ ID NO: 2) | mPD-L1 protein | 1.91 μM | 68 |
| | 4T1 cancer cell | 2.44 μM | 61 |
| CLP003 - (SEQ ID NO: 3) | mPD-L1 protein | 2.26 μM | 46 |
| | 4T1 cancer cell | 1.00 μM | 50 |
| CLP004 - (SEQ ID NO: 4) | mPD-L1 protein | 1.91 μM | 48 |
| | 4T1 cancer cell | 0.73 μM | 34 |

Figure 8A:
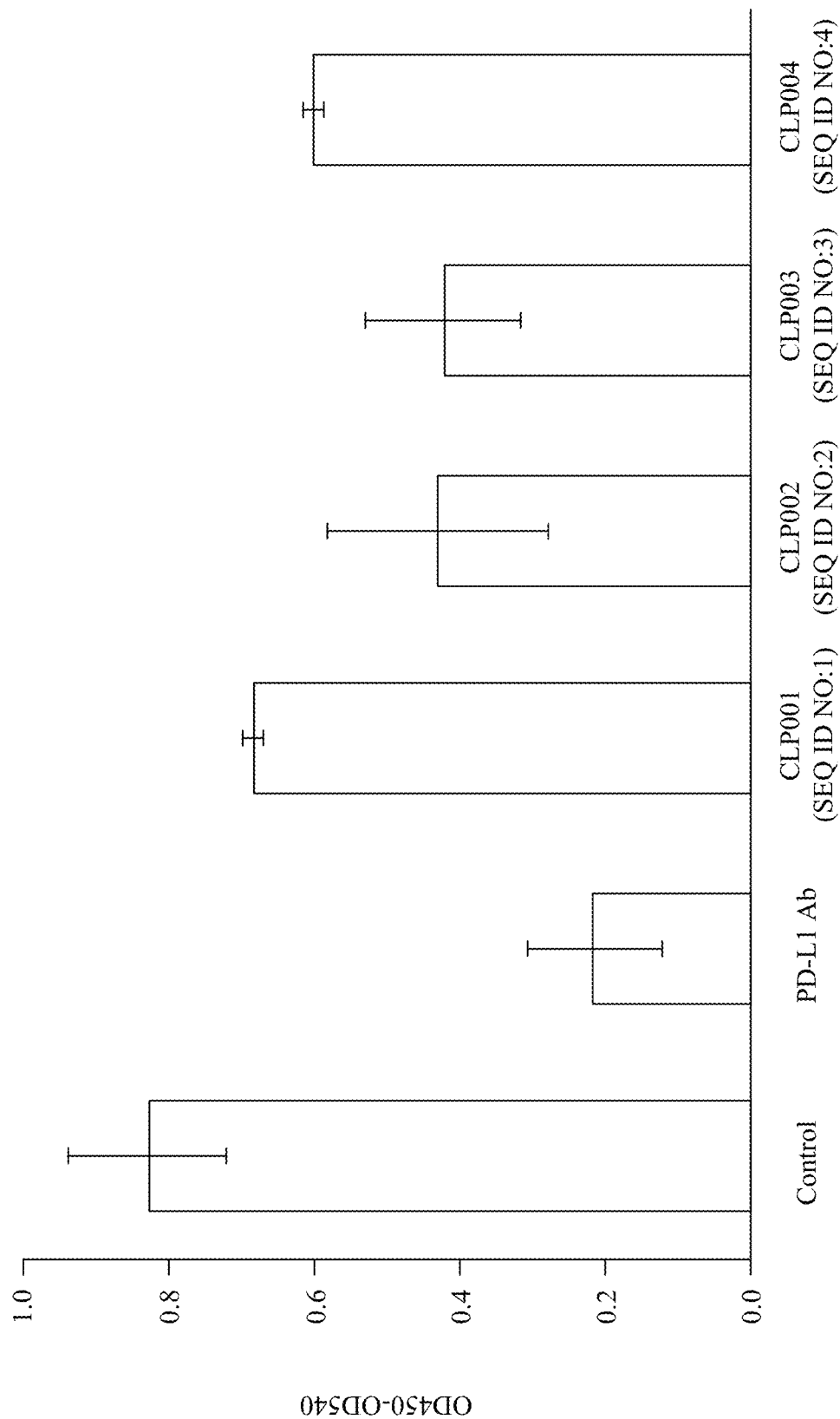
FIG. 8a is a graph depicting the blocking efficiency of the peptides and an anti-human PD-L1 antibody at 10 μM against the human PD-L1/CD80 interaction as detailed in Example 2, in accordance with aspects of the present disclosure.
Figure 8B:
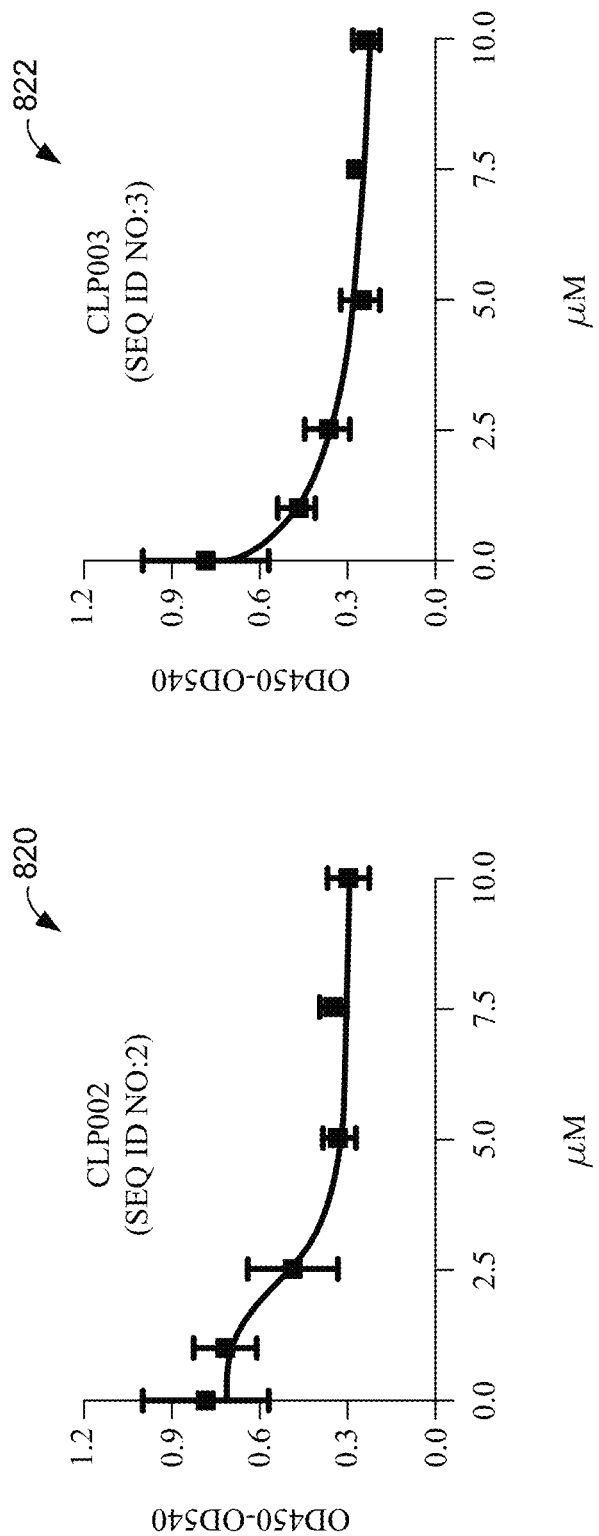
FIG. 8b is a series of graphs depicting the IC50 and blocking efficiency of certain peptides against the human PD-L1/CD80 interaction as detailed in Example 2, in accordance with aspects of the present disclosure.

It has been reported that PD-L1 binds to CD80 with a moderate binding affinity, and the CD80/PD-L1 interaction interface is partially overlapped with PD-1/PD-L1 and CD80/CTLA4 interfaces. The CD80/PD-L1 interaction specifically restrains T cell activation, and blockade of the interaction could enhance the anti-tumor activity of the T cells. For example, Durvalumab is a FDA-approved anti-PD-L1 antibody that blocks not only the PD-1/PD-L1 but also the CD80/PD-L1 interaction. In this Example, it was investigated whether the anti-PD-L1 peptides block the CD80/PD-L1 interaction. As revealed in FIG. 8a, we observed approximately 17%, 48%, 48% and 27% blocking efficiency of the peptides CLP001 (SEQ ID NO:1), CLP002 (SEQ ID NO:2), CLP003 (SEQ ID NO:3), and CLP004 (SEQ ID NO:4) at 10 μM (micromolar), respectively. The $IC_{50}$ values for the peptides CLP002 (SEQ ID NO:2)—graph 820—and CLP003 (SEQ ID NO:3)—graph 830—are 2.45 μM and 1.62 μM, respectively as shown in FIG. 8b. The data suggests that the anti-PD-L1 peptides block PD-1/PD-L1 and CD80/PD-L1 interactions simultaneously, leading to enhanced anti-tumor activity of the T cells.

Example 3: Molecular Docking for the Peptide/PD-L1 Interaction

Figure 3A:
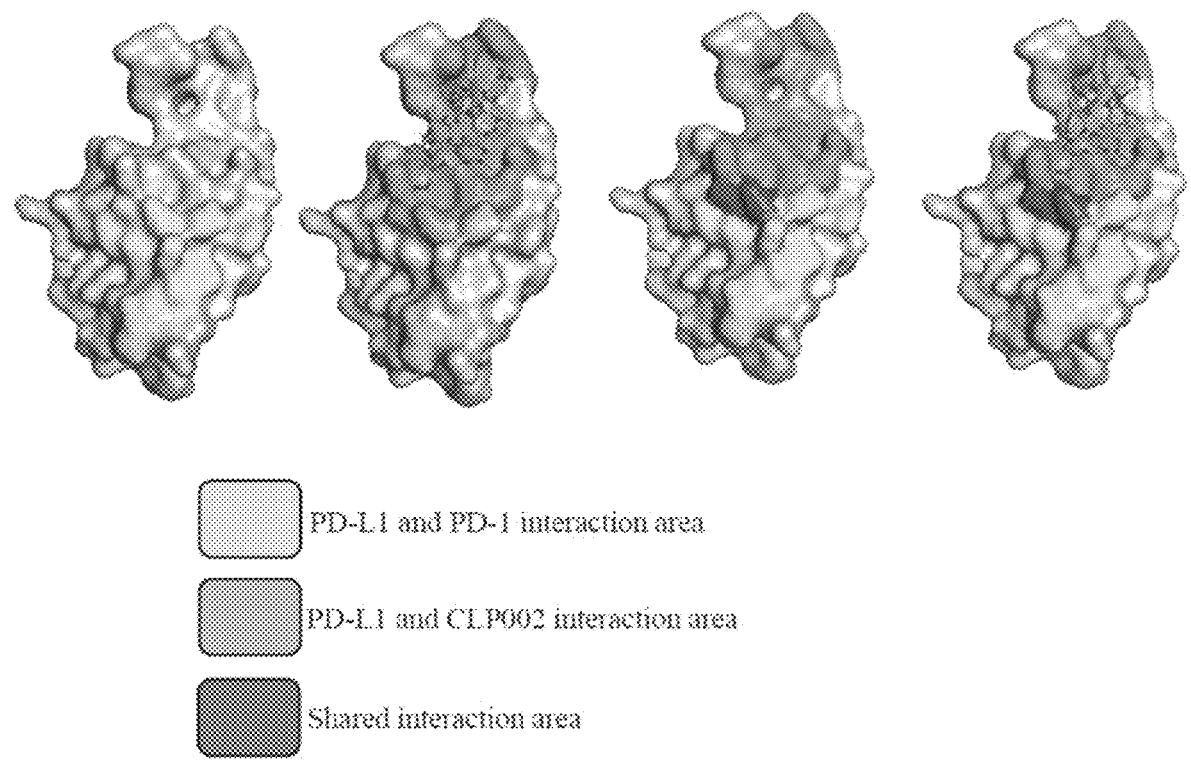
FIGS. 3a-3d are schematic depictions of the modeling and interaction between certain peptides and PD-L1 as detailed in Example 3, in accordance with aspects of the present disclosure.
Figure 3B:
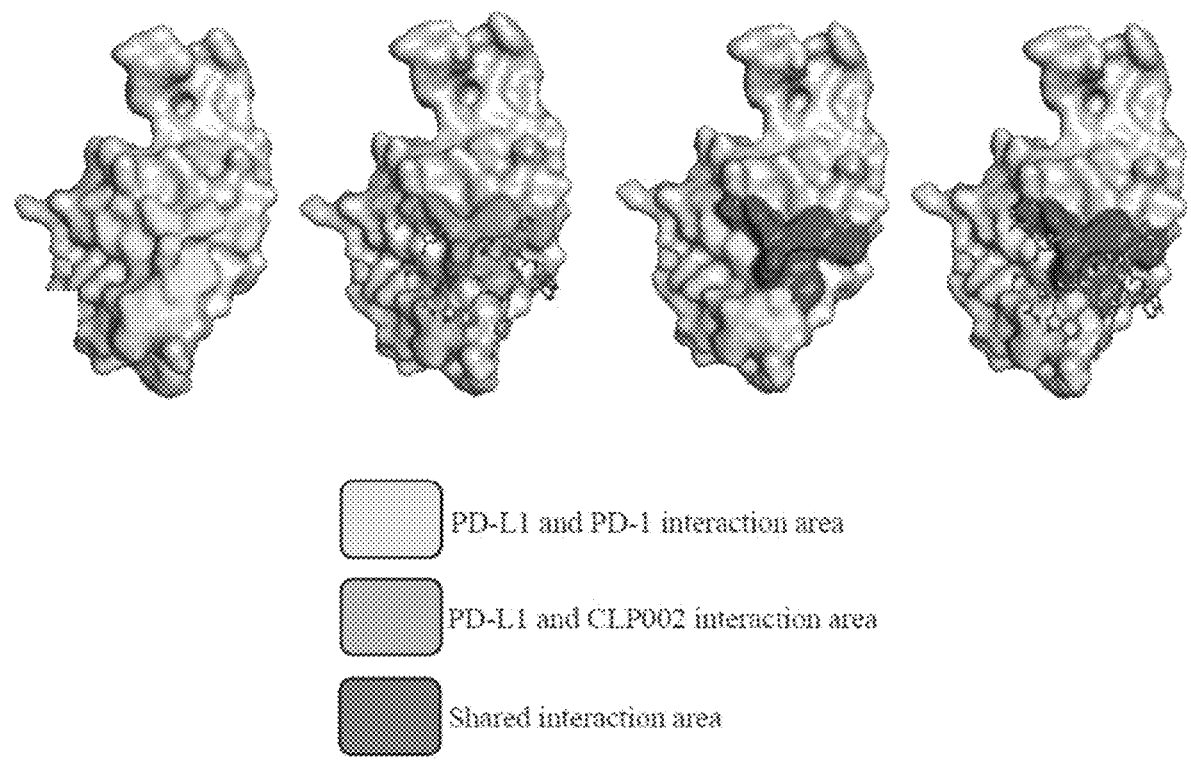
Figure 3C:
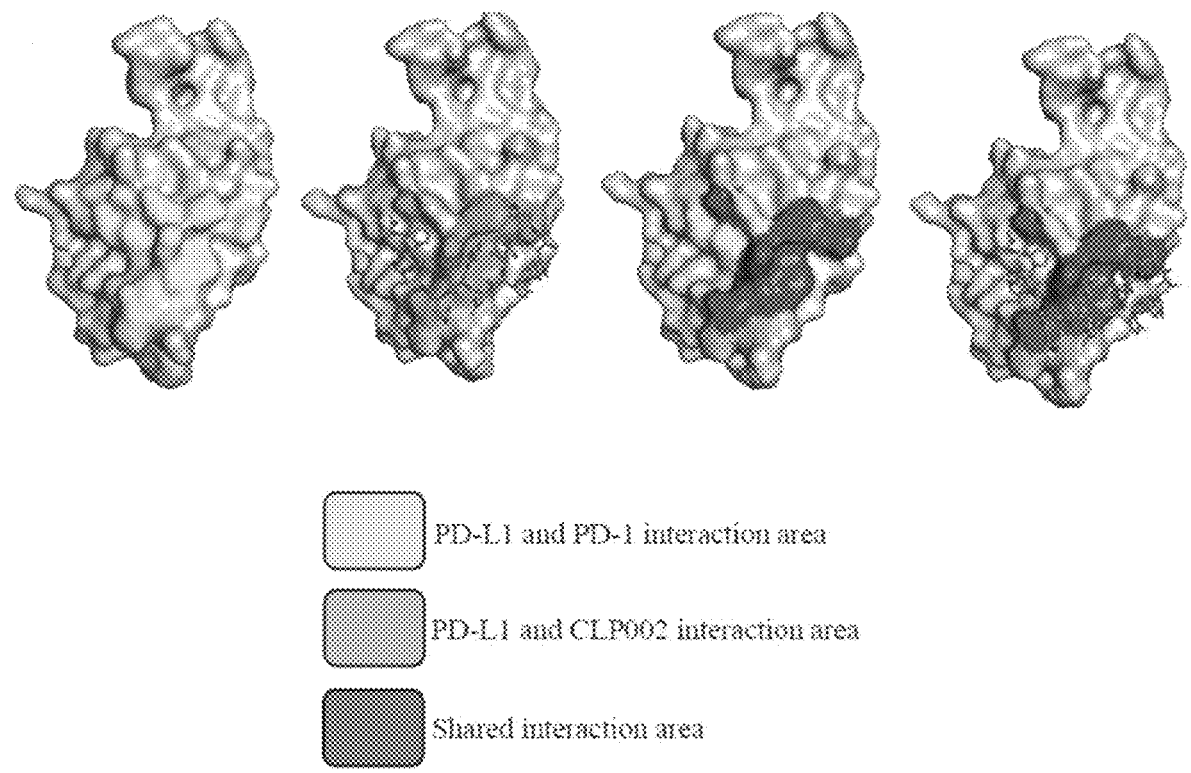
Figure 3D:
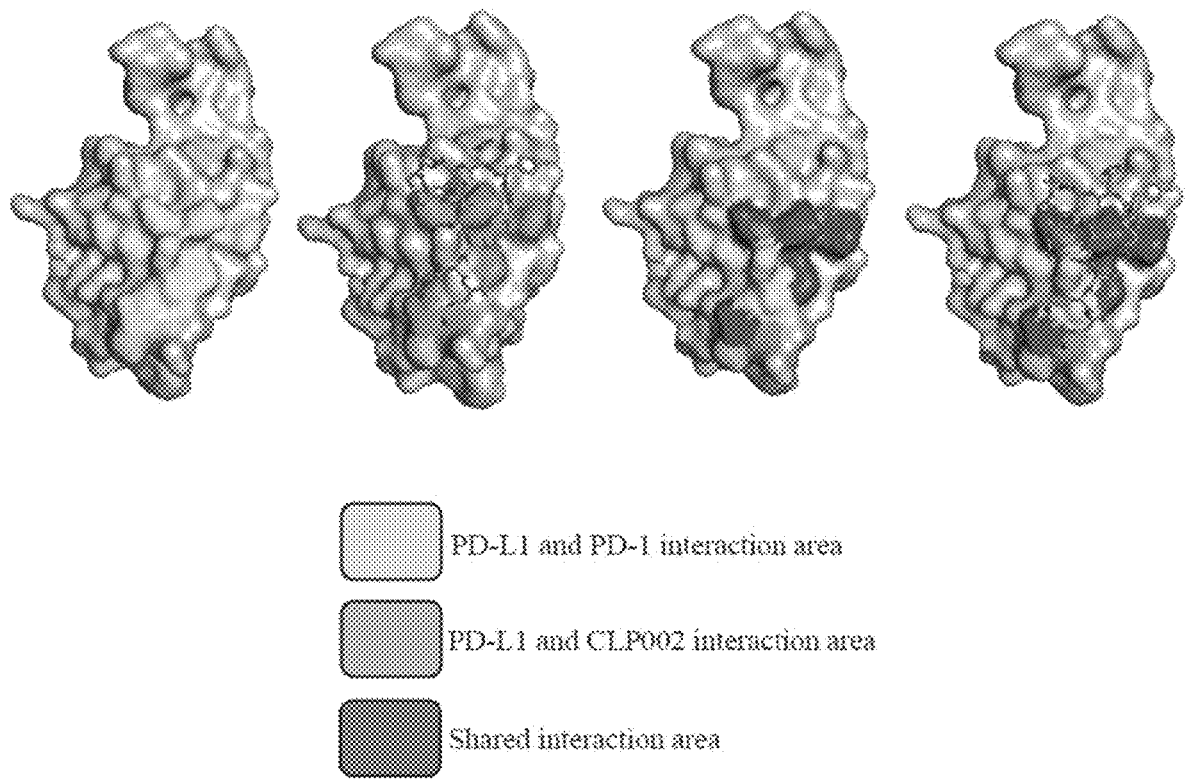

In this Example, molecular docking studies were performed to simulate the interactions between the anti-PD-L1 peptides and the human PD-L1 extracellular domain protein (PDB ID #5C3T) using Autodock Vina integrated into PyRx. Illustrations of the PD-L1/peptide complexes were generated using Pymol (FIGS. 3a-3d). The PD-L1 residues responsible for the PD-1/PD-L1 interaction were previously reported and highlighted in yellow. The binding residues of CLP002 (SEQ ID NO:2) and CLP003 (SEQ ID NO:3) on PD-L1 are highly overlapped with that of PD-1 (FIG. 3b, FIG. 3c). As illustrated in FIG. 3a, the CLP001 (SEQ ID NO:1) peptide does not bind to the PD-1/PD-L1 interaction residues, which explains the fact that the CLP001 (SEQ ID NO:1) peptide binds to PD-L1 but does not block the PD-L1/PD-1 interaction (FIG. 2e and Table 2). Similarly, there is only a small overlap between the CLP004 (SEQ ID NO:4)/PD-L1 binding area and the PD-L1/PD-1 interaction residues (FIG. 3d). This is also in accordance with the poor blocking efficacy of the CLP004 (SEQ ID NO:4) peptide in Example 2. In FIGS. 3a-3d, the PD-L1 residues responsible for peptide binding are highlighted in green; the binding residues for human PD-1 protein is highlighted in yellow; the overlapping PD-L1 residues for binding both anti-PD-L1 peptide, and PD-1 protein are highlighted in pink.

Example 4: CLP002 (SEQ ID NO:2) Restores T Cell Proliferation and Prevents T Cell Apoptosis in the Presence of PD-L1-Overexpressing Cancer Cells In the tumor microenvironment, PD-L1-overexpressing tumor cells inhibit T cell activation and promote T cell apoptosis, leading to exhausted phenotype and impaired effector function of the T cells. The PD-1/PD-L1 interaction also suppresses T cell proliferation and inhibits the secretion of inflammatory cytokines. Thus, in this example, Jurkat T cells were co-cultured with PD-L1-overexpressing DU-145 cancer cells to investigate whether the anti-PD-L1 peptides reverse the inhibitory effect of DU-145 cancer cells on Jurkat T cells.

Figure 4A:
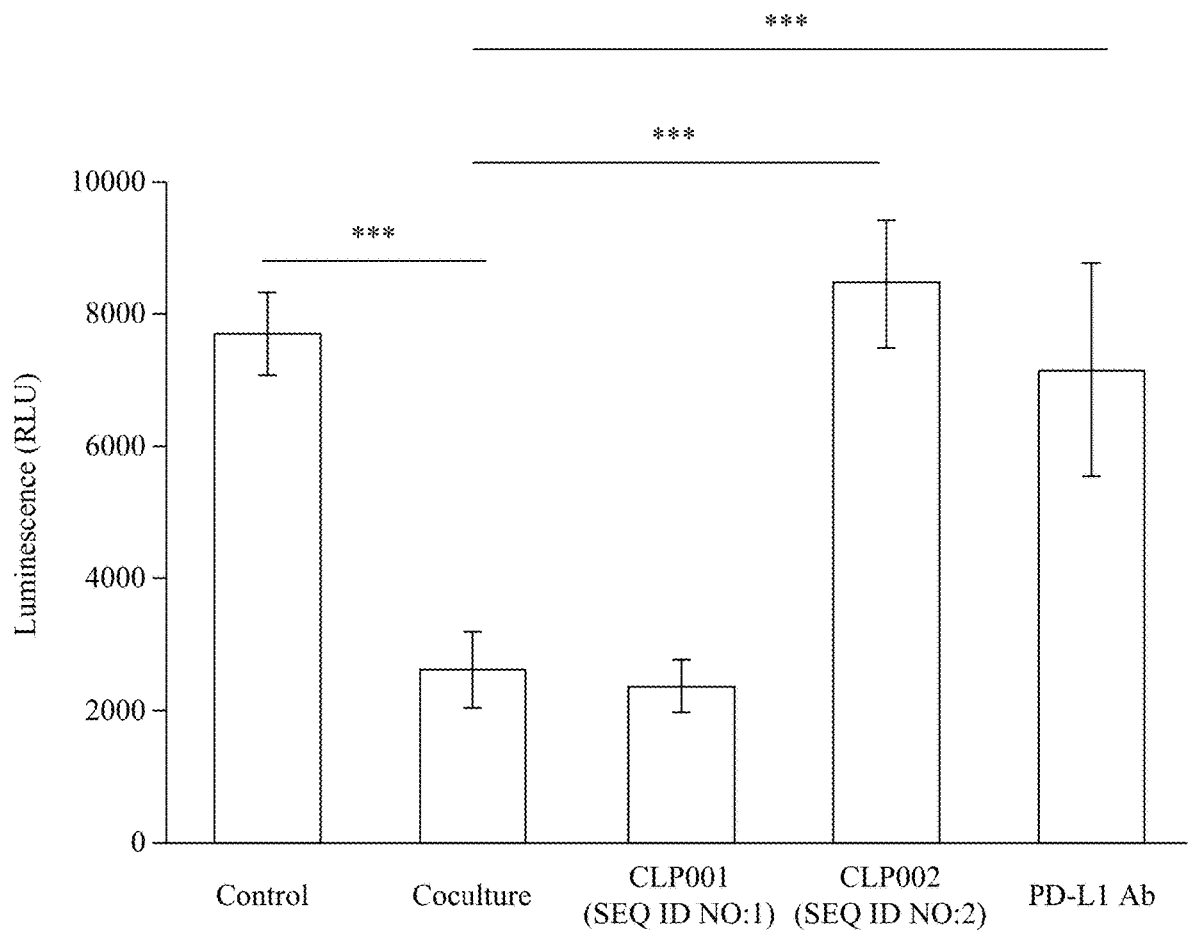
FIG. 4a is a graph depicting T cell proliferation restoration with certain peptides as detailed in Example 4, in accordance with aspects of the present disclosure.

As can be seen in FIG. 4a, DU-145 cells significantly inhibited T cell proliferation through the PD-1/PD-L1 interaction. Treatment of the co-cultured cells with the CLP002 (SEQ ID NO:2) peptide restored Jurkat T cell proliferation. The co-cultured cells were also treated with the CLP001 (SEQ ID NO:1) peptide but did not observe the same effect on T cells (FIG. 4a). This is in agreement with our finding that the CLP001 (SEQ ID NO:1) peptide is not able to block the human PD-1/PD-L1 interaction (Example 2 above). These results further proved that PD-L1-overexpressing cancer cells inhibit the proliferation of Jurkat cells through the PD-1/PD-L1 interaction.

Figure 4B:
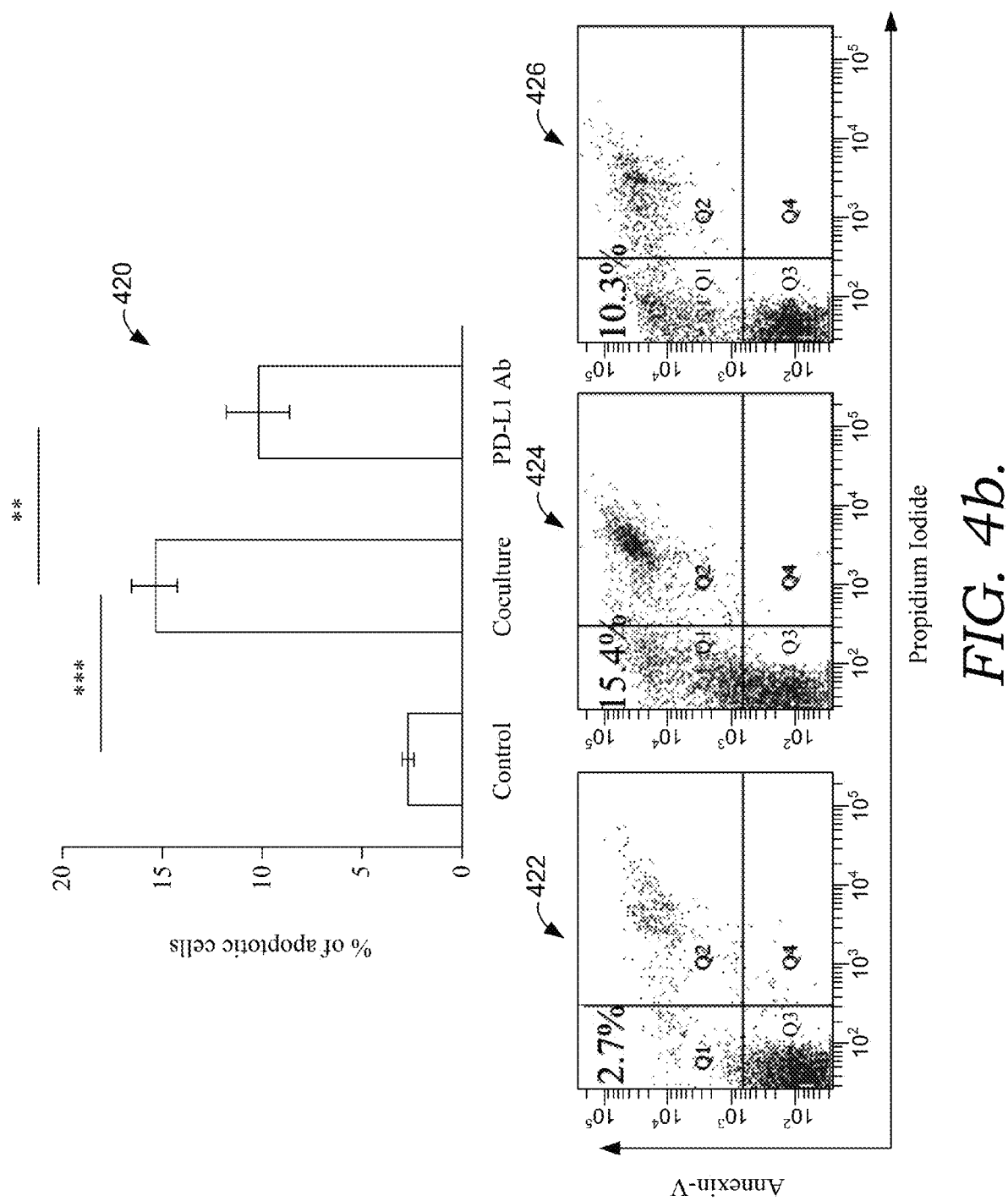
FIGS. 4b and 4c depict a series of graphs showing a reduction in T cell apoptosis with certain peptides or an anti PD-L1 antibody as detailed in Example 4, in accordance with aspects of the present disclosure.
Figure 4C:
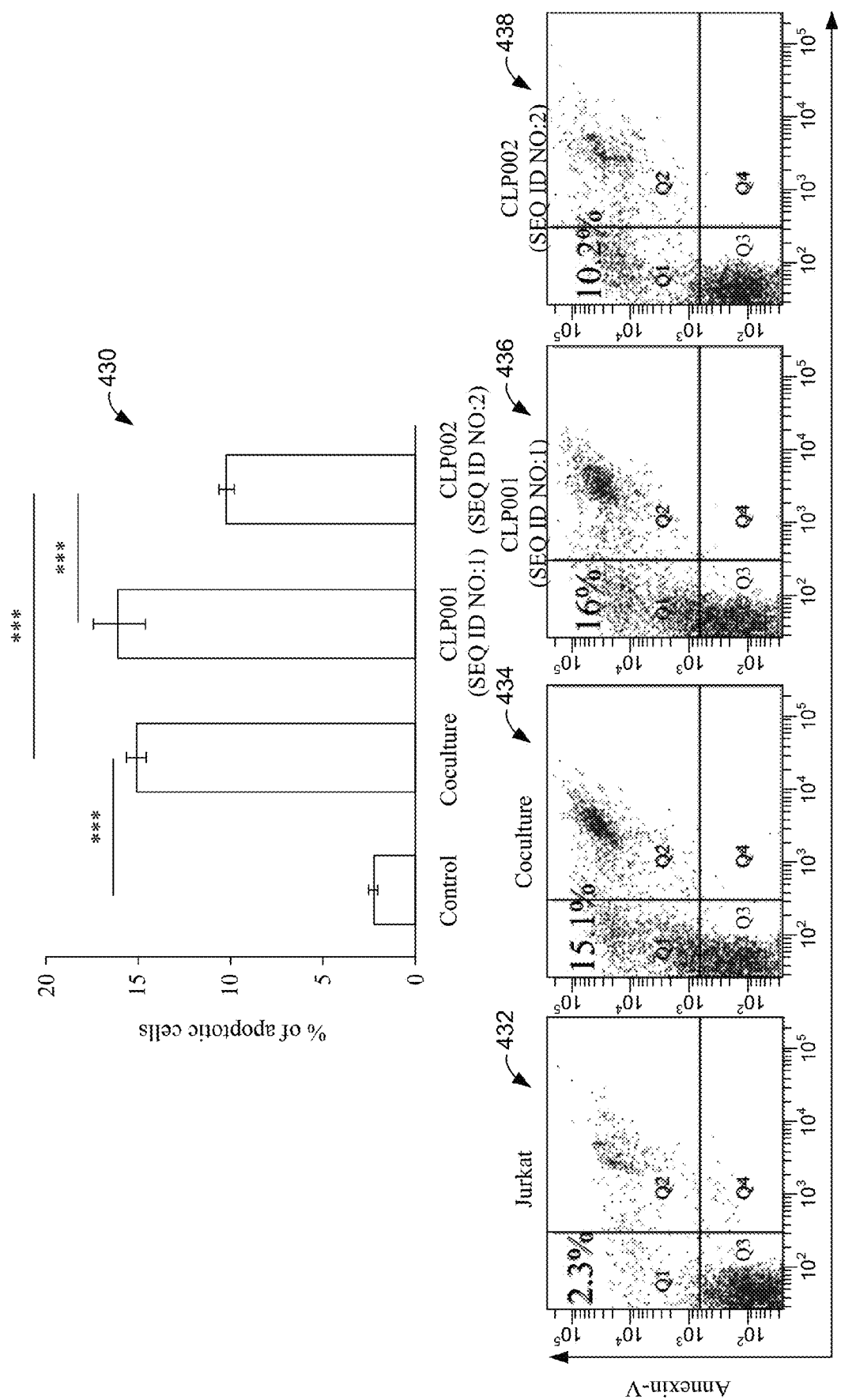

This Example also investigated the effect of the anti-PD-L1 peptides and anti-PD-L1 antibody on the apoptosis of Jurkat cells in the presence of DU-145 cells. As shown in FIGS. 4b and 4c and the graphs 420, 422, 424, 426, 430, 432, 434, 436, and 438 therein, the apoptosis of Jurkat cells increased from 2.3% to 15.1%, when the cells were co-cultured with DU-145 cells. In FIGS. 4a, 4b, and 4c, the results are represented as the mean±SD (n=3). ( $p<0.01$; * $p<0.001$). Apoptosis was effectively inhibited to 10.2% and 10.3% when the co-cultured cells were treated with the CLP002 (SEQ ID NO:2) peptide or anti PD-L1 antibody but not the CLP001 (SEQ ID NO:1) peptide. This result is in agreement with the proliferation assay (FIG. 4a). In this Example, increased apoptosis was observed of cytotoxic T lymphocytes after incubation with melanoma cancer cells. However, apoptosis of the immune cells was not observed, when PD-L1 was knocked out in melanoma tumor cells. In addition, tumor-promoted T cell apoptosis was significantly reduced by incubating with an anti-PD-1 antibody.

Figure 5A:
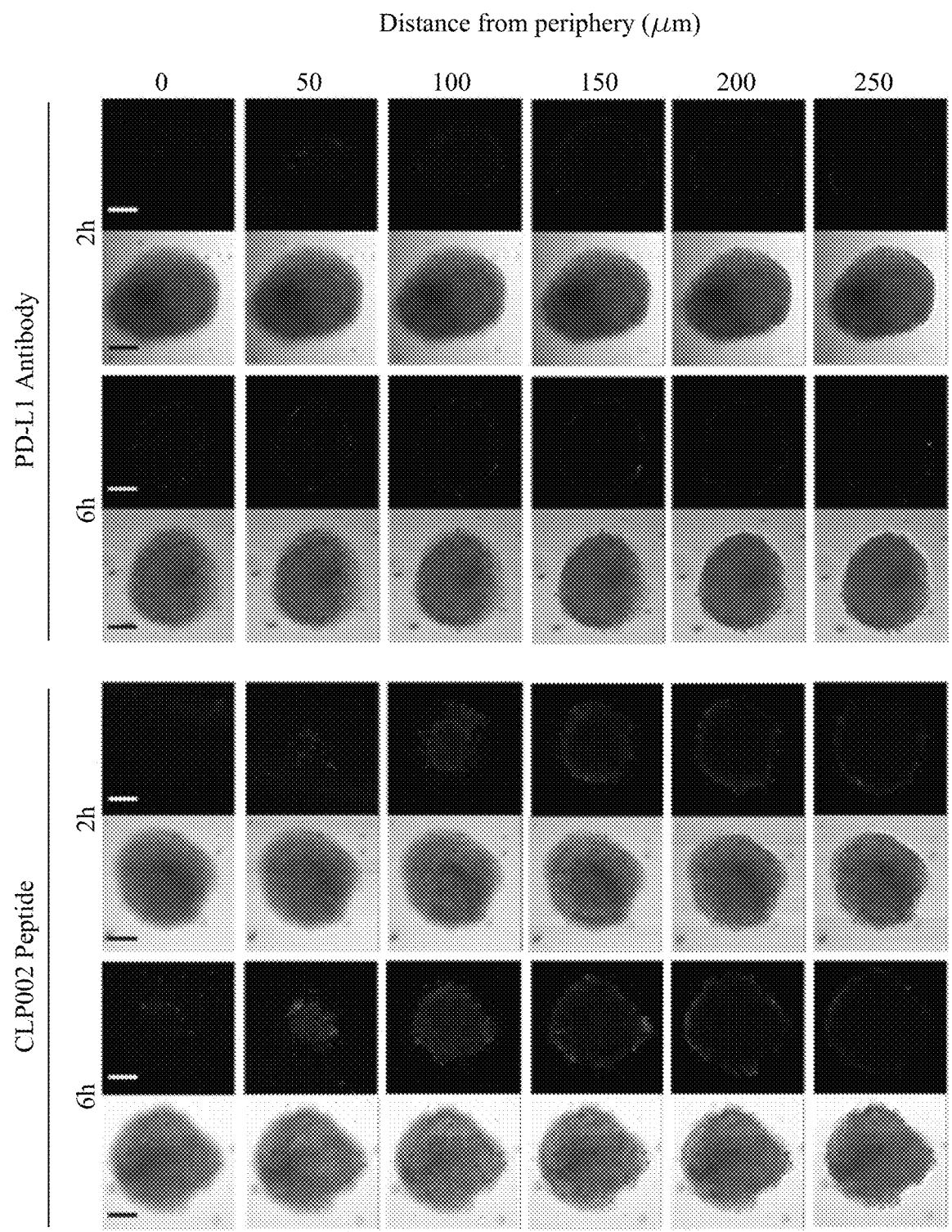
FIG. 5a is a series of images depicting representative Z stacked confocal images of 3D tumor spheroids of MDA-MB-231 cells with a z-step of 50 μm, with the scale bar representing 200 μm to compare the tumor penetration capability of a certain peptide and an anti-PD-L1 antibody as detailed in Example 5, in accordance with aspects of the present disclosure.
Figure 5B:
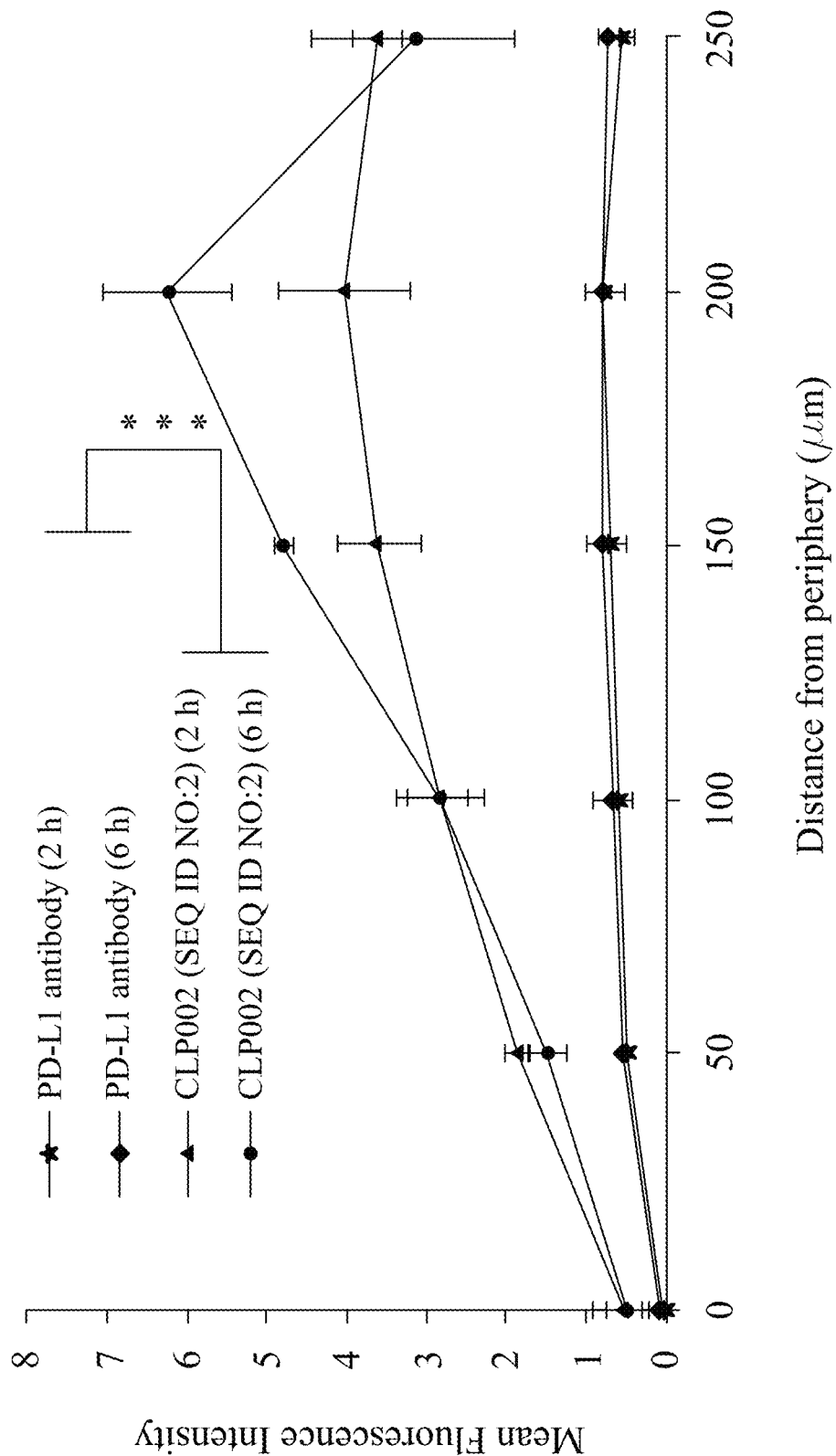
FIG. 5b is a graph depicting the quantification of the depth penetration of the certain peptide and anti-PD-L1 antibody of the images from FIG. 5a, in accordance with aspects of the present disclosure.

Example 5: Comparison of Tumor Penetration of the Anti-PD-L1 Peptide CLP002 (SEQ ID NO:2) and Anti-PD-L1 Antibody It is thought that low-molecular-weight peptides have better tumor penetration than antibodies, which may lead to improved therapeutic efficacy. A 3D tumor spheroid model of MDA-MB-231 cells was developed to compare tumor penetration of the CLP002 (SEQ ID NO:2) peptide and the anti-PD-L1 antibody (29E.2A3, BioXcell, West Lebanon, N.H.). Cy5-labeled peptide and antibody were incubated with the tumor spheroids (~700 µm in diameter) for 2 and 6 hours, followed by confocal microscopy analysis to evaluate tumor penetration. FIG. 5a shows representative Z-stacked confocal images of the spheroids with a z-step of 50 µm. The scale bar represents 200 µm. FIG. 5b is a graph depicting the depth of penetration is quantified by mean fluorescence intensity. Results are represented as the mean±SD (n=3). As illustrated in FIGS. 5a-5b, the CLP002 (SEQ ID NO:2) peptide exhibited better tumor penetration than the antibody. Fluorescence of the Cy5-labeled CLP002 (SEQ ID NO:2) peptide was detected as deep as approximately 250 µm from the periphery of the spheroids. By contrast, Cy5-labeled antibody was only detected on the periphery of the spheroids, suggesting very limited tumor penetration.

In this Example, higher tumor penetration of a low-molecular-weight peptide compared to its counterpart antibody in a 3D tumor spheroid model was demonstrated. Incomplete penetration into the tumor is a major limitation for macromolecular therapeutics, such as antibodies. The penetration rate of a macromolecule is highly dependent on its molecular size and binding affinity to tumor cells. While tumor penetration is inversely correlated to macromolecule's molecular size, the correlation between tumor penetration and macromolecule's affinity can be complicated. Without being bound by any particular theory, it is generally believed that increasing the affinity of a macromolecule leads to enhanced tumor retention. However, the very high binding affinity of an antibody prevent its tumor penetration because of the "binding site barrier" effect. The antibody strongly binds to tumor cell surface but cannot diffuse into the tumor microenvironment. Compared to antibodies, peptides pertain much smaller size and relatively lower binding affinity, which lead to better tumor spheroid penetration, as is evidenced in this Example.

Example 6: Anti-Tumor Activity of the Anti-PD-L1 Peptides and Antibody

Figure 6A:
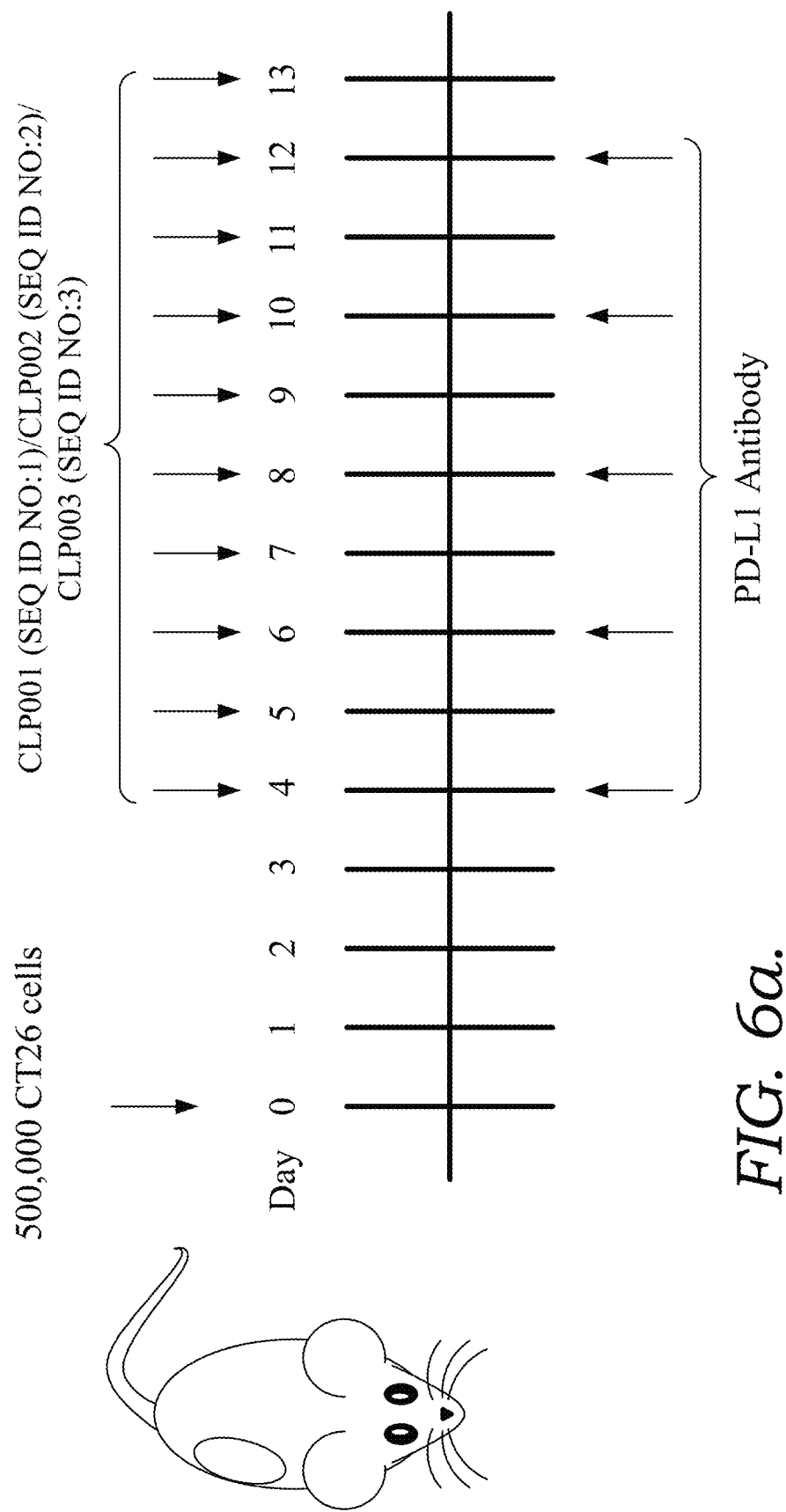
FIG. 6a is a schematic depiction of an experimental setup to investigate the anti-tumor activity of certain peptides and an antibody in CT26 bearing Balb/C mice and is further described in Example 6, in accordance with aspects of the present disclosure.
Figure 6B:
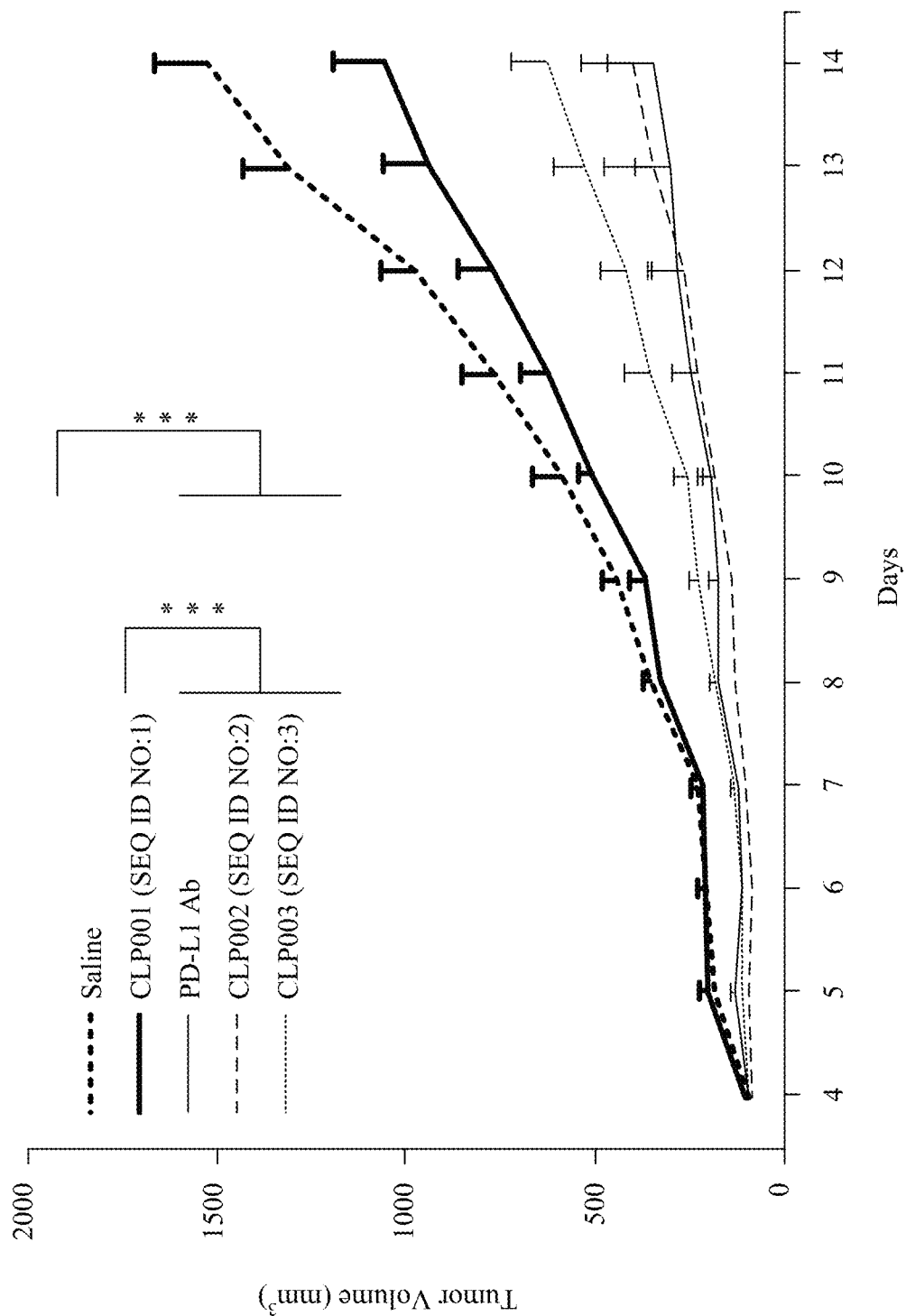
FIG. 6b is a graph depicting the CT26 tumor volume from certain peptides and the antibody in the experiment schematically depicted in FIG. 6A, in accordance with aspects of the present disclosure.
Figure 6C:
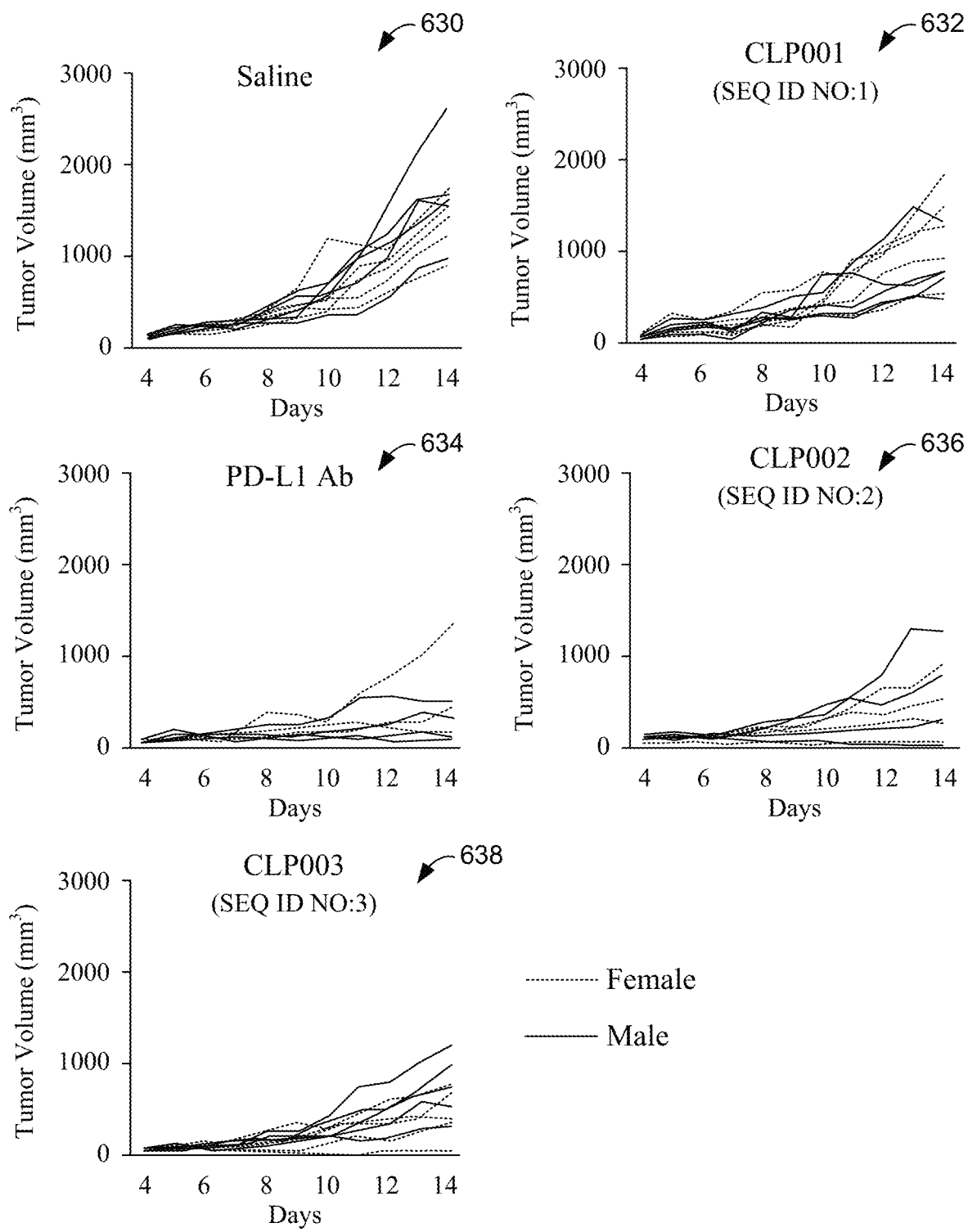
FIG. 6c is a series of graphs depicting the CT26 tumor growth curves of individual mice in each labeled group in the experiment schematically depicted in FIG. 6a, in accordance with aspects of the present disclosure.
Figure 6D:
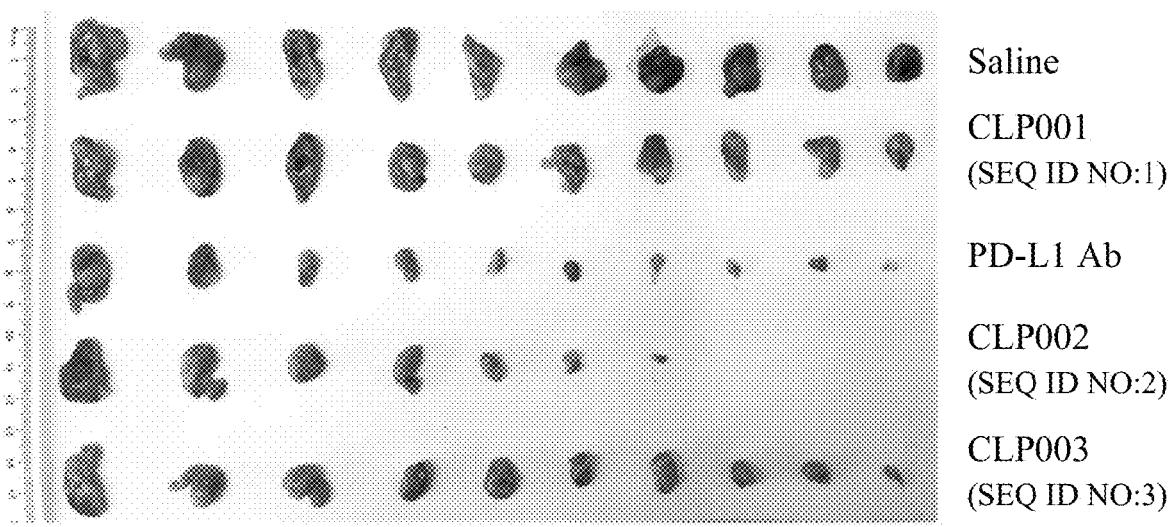
FIG. 6d is a series of images depicting the CT26 tumors harvested on day 14 from the experiment schematically depicted in FIG. 6a, in accordance with aspects of the present disclosure.
Figure 6E:
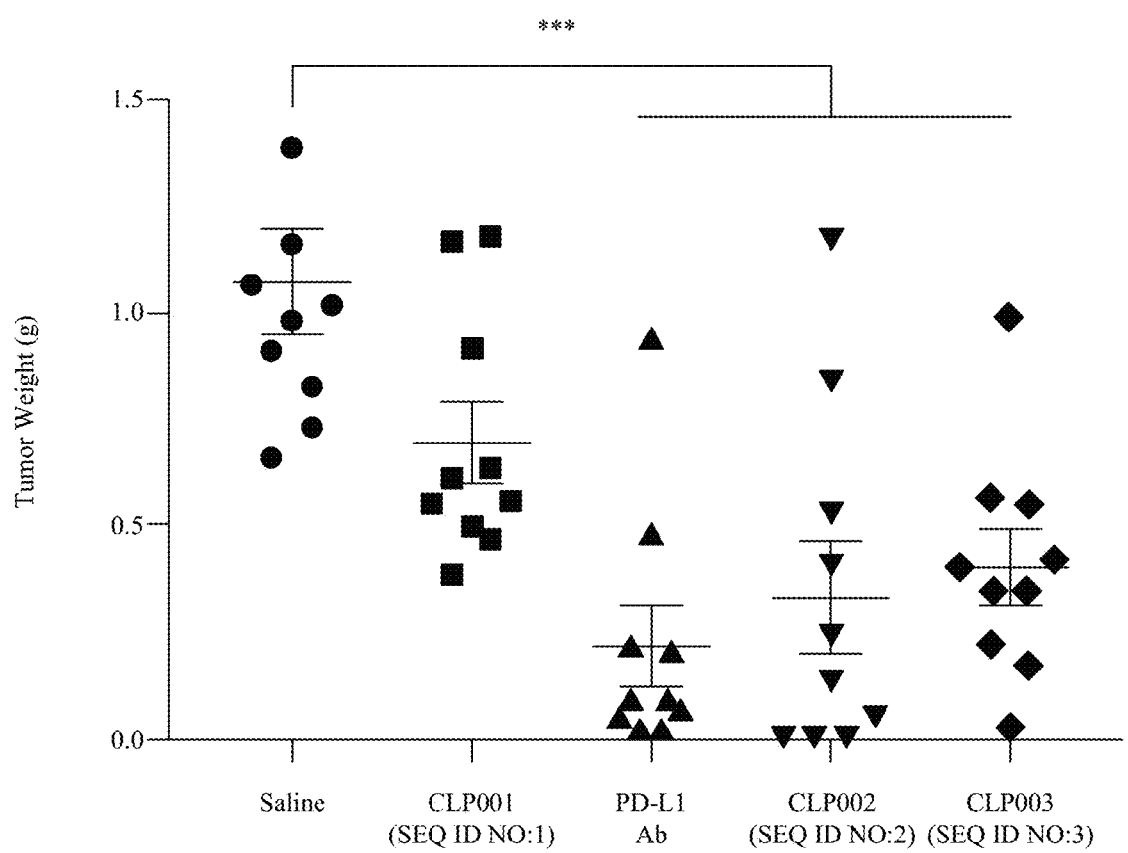
FIG. 6e is a graph depicting the mass of the CT26 tumors harvested on day 14 from the experiment schematically depicted in FIG. 6a, in accordance with aspects of the present disclosure.

The antitumor activity of the anti-PD-L1 peptides using the CT26 colorectal tumor-bearing mouse model (FIG. 6a) was evaluated in this Example, which has been widely used to evaluate the activity of PD-1/PD-L1 inhibitors. As can be seen in FIG. 6a, CT26 tumor-bearing Balb/C mice (n=10, 5 male and 5 female) were intraperitoneally injected with the anti-PD-L1 peptides (2 mg/Kg) daily for a total of 10 injections and the anti-mouse PD-L1 antibody (10 mg/Kg) every other day for a total of 5 injections. Once the average tumor volume reached 50-100 mm$^3$, the peptides (2 mg/kg) were administrated intraperitoneally daily, as described in a previous study (Chang, H. N. et al. Blocking of the PD-1/PD-L1 Interaction by a D-Peptide Antagonist for Cancer Immunotherapy. *Angew Chem Int Ed Eng/*54, 11760-11764 (2015)). The anti-mouse PD-L1 antibody (BioXcell, 10F.9G2) was administered intraperitoneally every other day at 10 mg/kg. As FIGS. 6b to 6d and graphs 630, 632, 634, 636, and 638 in FIG. 6c show, CLP002 (SEQ ID NO:2), CLP003 (SEQ ID NO:3), and the antibody effectively suppressed tumor growth. As shown in FIG. 6e, the tumor weights of the PD-L1 antibody, CLP002 (SEQ ID NO:2) and CLP003 (SEQ ID NO:3) group were significantly smaller than the saline group. In general, CLP002 (SEQ ID NO:2) exerted a better tumor inhibitory effect than CLP003 (SEQ ID NO:3), which was similar to the antibody. FIG. 6b shows tumor volume measured over time and are represented as the mean±SE (n=10). FIG. 6c shows tumor growth curves of individual mice in each group. FIG. 6d shows images of tumors at various days, ending at day 14. In FIG. 6e the weight of the tumors harvested at day 14 is shown. The results were represented as the mean±SD (n=10). It is noteworthy that the peptides were screened against the human PD-L1 protein, which, in fact, would compromise the anti-tumor activity of the peptides in a mouse model. Thus, these peptides may also exhibit anti-tumor activity in human cancer cells.

Figure 6F:
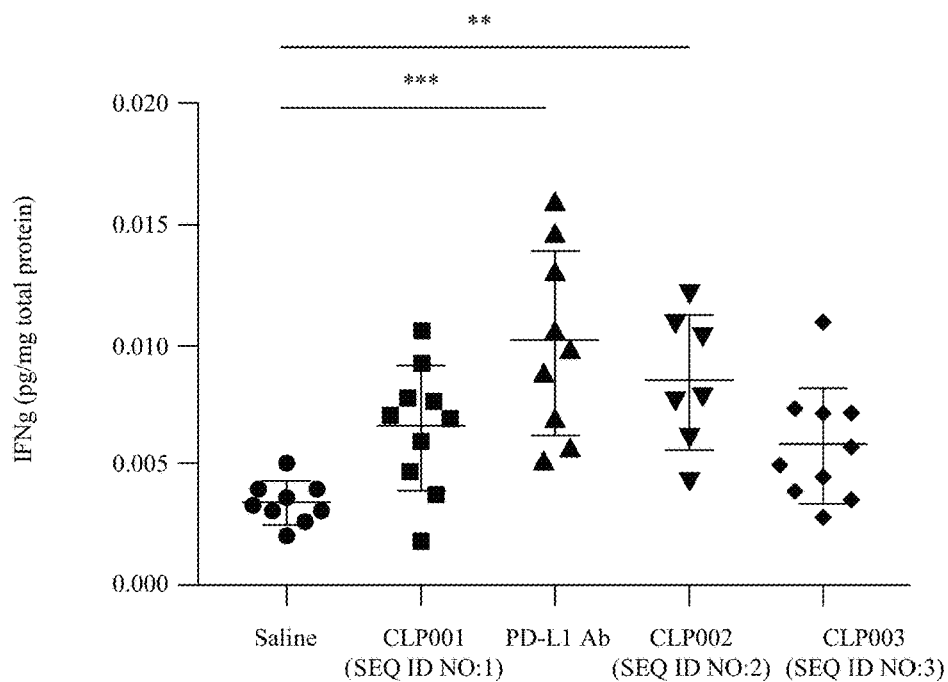
FIGS. 6f-6h is a series of graphs depicting the expression of various markers or proteins in the harvested tumors from the experiment schematically depicted in FIG. 6a, in accordance with aspects of the present disclosure.
Figure 6G:
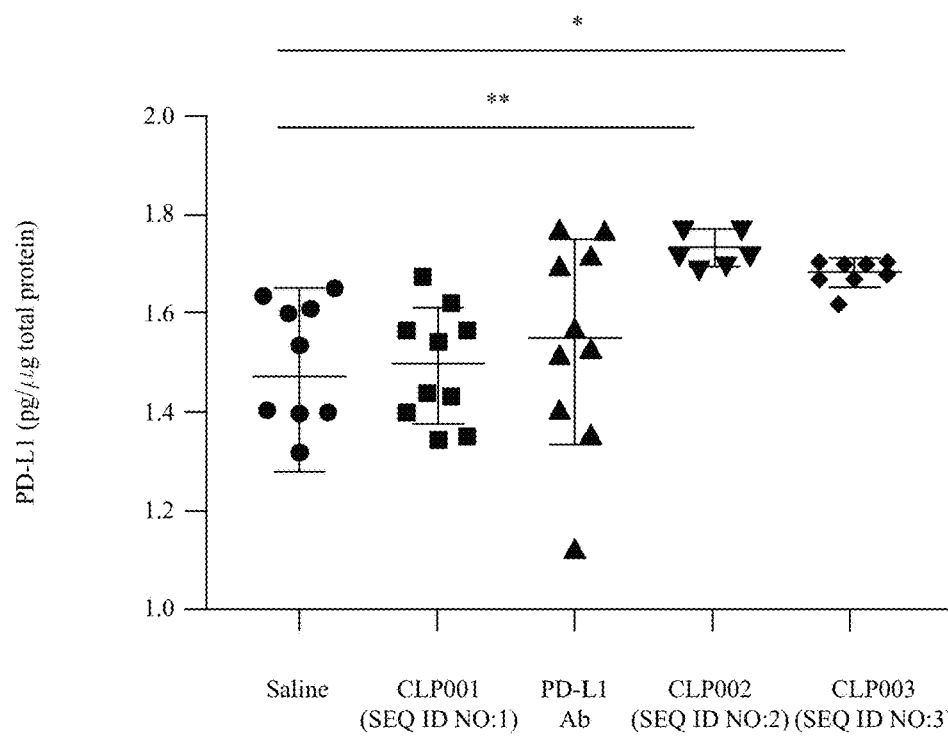

The expressions of PD-L1 and cytokines associated with anti-tumor immune responses were also evaluated in this Example. IFNγ is a multifunctional cytokine secreted by activated T cells. It was generally thought that the therapeutic effect of cytotoxic T cells is mainly mediated by the secretion of IFNγ. However, IFNγ may also upregulate PD-L1 expression on cancer cells to escape T cell-mediated immune response. In this Example, upregulated IFNγ and PD-L1 levels in the tumors after the treatment with the anti-PD-L1 antibody and the peptides was observed (FIGS. 6f and 6g). Because IFNγ induces the expression of PD-L1 on tumor cells, slightly higher PD-L1 levels of the treated tumor tissue were also observed. As has been reported, IFNγ initially triggers immune response through the T cell activation. PD-L1 expression was also elevated by secreted IFNγ, which facilitates the escape of tumors from T cell-mediated immune response.

Figure 6H:
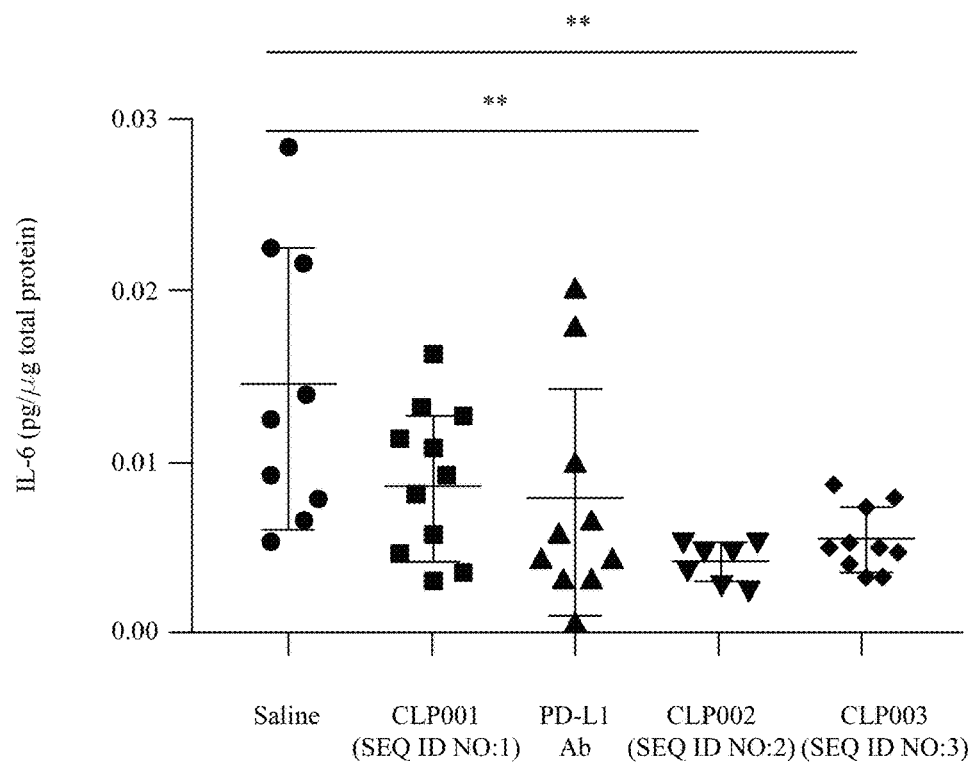

IL-6 is often upregulated along with tumor growth. For example, prominent IL-6 expression was detected in pancreatic tumor microenvironment, which is critical for tumor progression (Mace, T. A. et al. IL-6 and PD-L1 antibody blockade combination therapy reduces tumor progression in murine models of pancreatic cancer. Gut 67, 320-332 (2018)). The IL-6/STAT3 pathway facilitates the expansion of immunosuppressive cells or changes the balance of T cell subsets, such as T regulatory cells and MDSCs, which promote tumor growth. Blockade of IL-6 with an antibody inhibits tumor growth and enhances survival in mice bearing aggressive pancreatic cancer cells. In a clinical study, the expression of IL-6 in the blood was found to be reduced in cancer patients who received the treatment of the anti-PD-L1 antibody MPDL3280A (Herbst, R. S. et al. Predictive correlates of response to the anti-PD-L1 antibody MPDL3280A in cancer patients. Nature 515, 563-567 (2014)). In agreement with these reports, a decreased expression of IL-6 in the tumor tissues after the treatment with CLP002 (SEQ ID NO:2) and CLP003 (SEQ ID NO:3) was observed (see FIG. 6h). For FIGS. 6f, 6g, and 6h, the expressions of IFNγ, PD-L1, and IL-6 in harvested tumors were measured using ELISA.

Figure 6I:
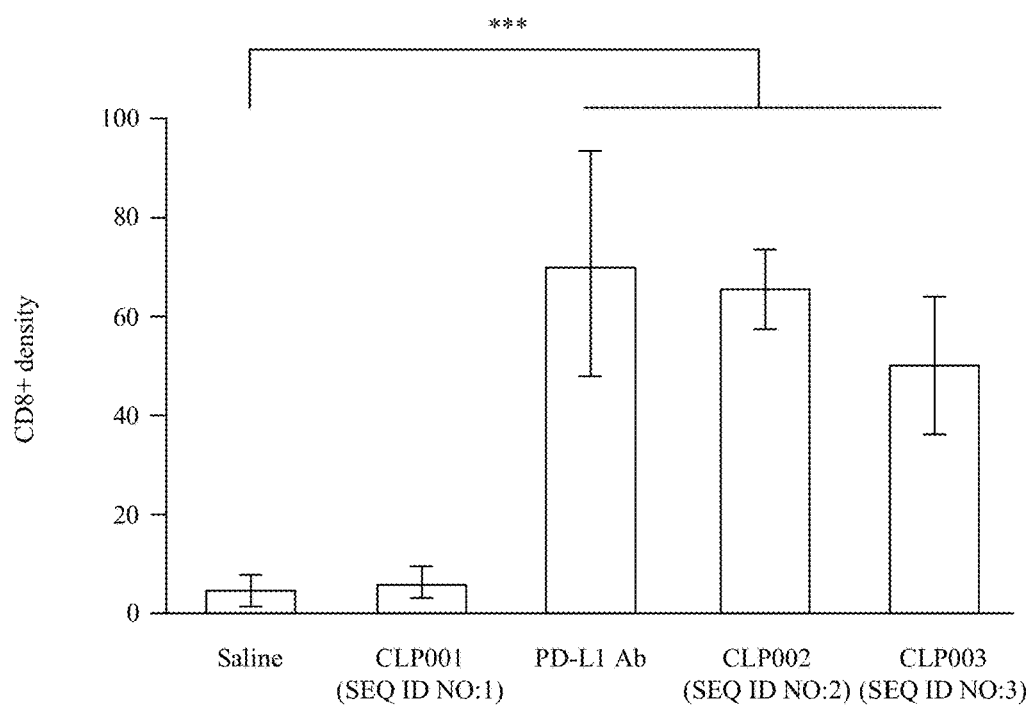
FIG. 6i is a graph depicting the number of CD8+ cells in each specimen from the experiment schematically depicted in FIG. 6a, in accordance with aspects of the present disclosure.
Figure 6J:
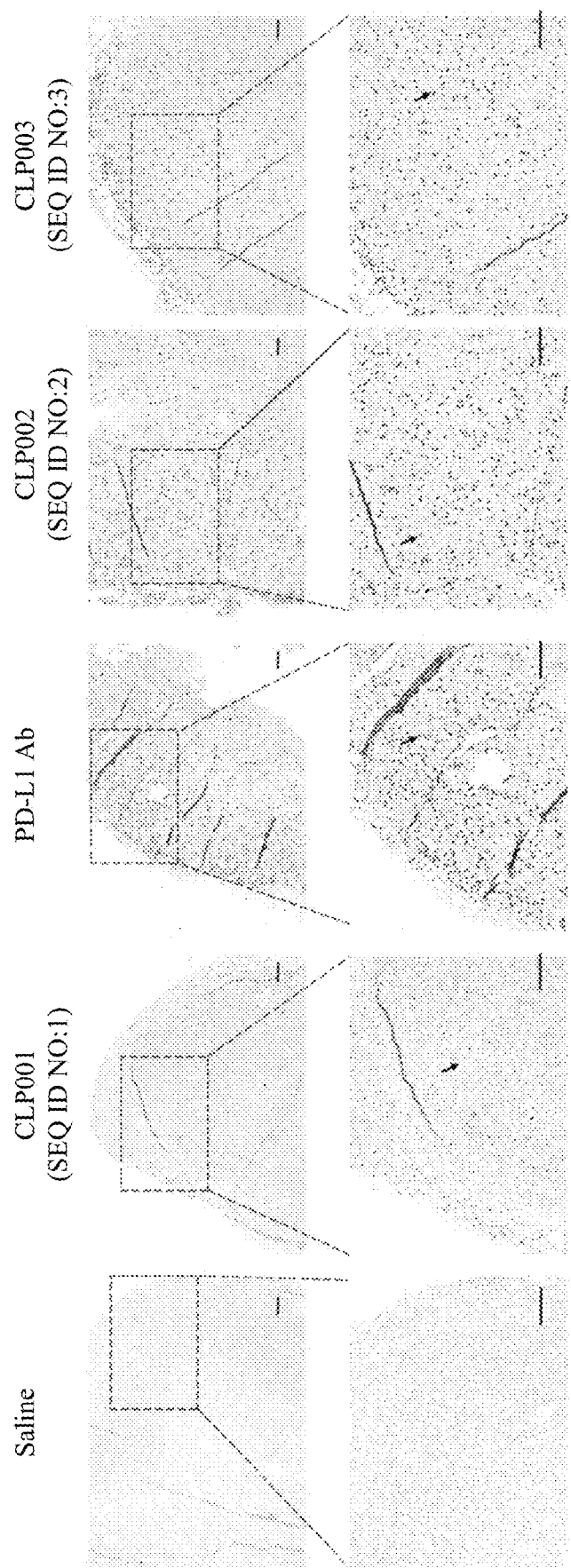
FIG. 6j is a series of images of certain tumor specimens from the experiment schematically depicted in FIG. 6a stained with anti-CD8 antibody, in accordance with aspects of the present disclosure.

CD8$^+$ cytotoxic T lymphocytes play critical roles in cancer immunotherapy using checkpoint inhibitors. In this Example, immunohistochemical staining for CD8$^+$ T cells in the tumor tissues was investigated. In agreement with previous reports, both the antibody and the anti-PD-L1 peptides (CLP002 (SEQ ID NO:2) and CLP003 (SEQ ID NO:3)) significantly increased the density of CD8$^+$ T cells in tumor tissues (see FIGS. 6i and 6j). In addition, penetration of CD8$^+$ T cells into the tumor tissue of CLP002 (SEQ ID NO:2)-treated mice was observed. By contrast, CD8$^+$ T cells were mainly detected on the periphery of the tumors in PD-L1 antibody treated mice. This could be due to the better tumor penetration of the peptides (as shown in Example 5), which promote the infiltration or proliferation of CD8$^+$ T cells. The numbers of CD8$^+$ T cells in each specimen were quantitated after immunohistochemical staining. Results were represented as the mean±SD (n=4). FIG. 6j shows representative images of tumor specimen stained with anti-CD8 antibody. The scale bar represents 200 μm. (* p<0.05;  p<0.01; * p<0.001).

Figure 7A:
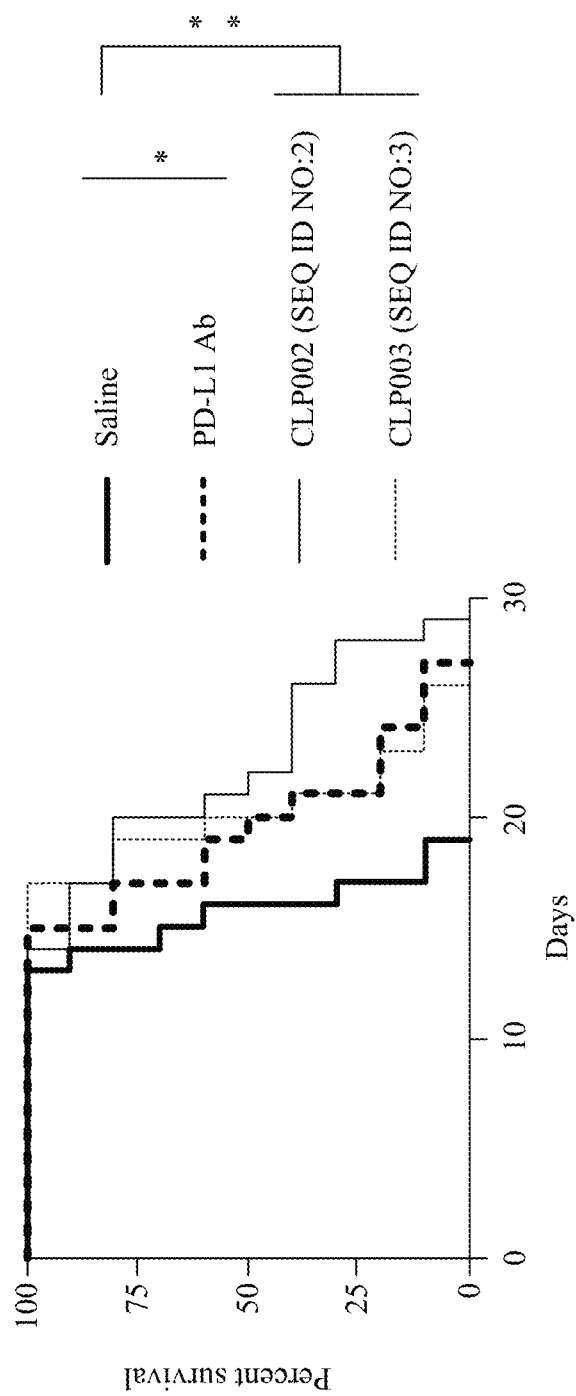
FIG. 7a depicts survival curves of various CT26 tumor-bearing Balb/C mice (that were intraperitoneally injected with certain anti-PD-L1 peptides and an anti-mouse PD-L1 antibody described in Example 7), in accordance with aspects of the present disclosure.
Figure 7B:
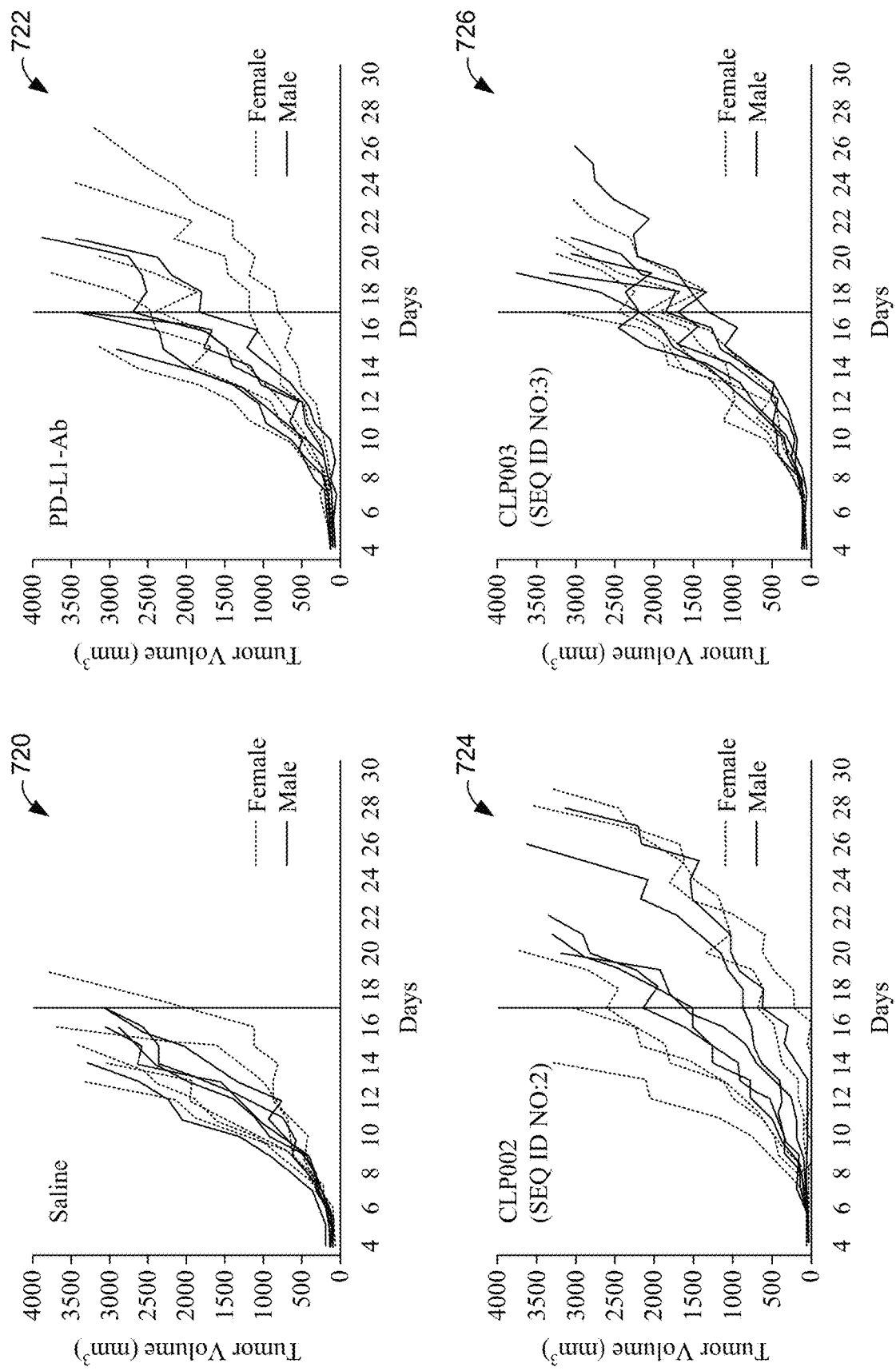
FIG. 7b is a series of graphs depicting tumor growth curves of individual mice from the experiment described in Example 7, in accordance with aspects of the present disclosure.

Example 7: Survival Curves of the Mice Treated with the Anti-PD-L1 Peptides and PD-L1 Antibody In this Example, mice were intraperitoneally injected with the CLP002 (SEQ ID NO:2) and CLP003 (SEQ ID NO:3) peptides daily or the anti-mouse PD-L1 antibody every other day from day 4 to day 17 (see survival curves in FIG. 7a). Specifically, CT26 tumor-bearing Balb/C mice (n=10, 5 male and 5 female) were intraperitoneally injected with the anti-PD-L1 peptides (2 mg/Kg) daily and the anti-mouse PD-L1 antibody (10 mg/Kg) every other day from day 4 to day 17. GraphPad Prism 7 software (San Diego, Calif.) was used for statistical analysis. Comparison of two survival curves were conducted using the Gehan-Breslow-Wilcoxon test. CLP002 (SEQ ID NO:2) inhibited tumor growth and improved the survival of tumor-bearing mice compared with control animals. CLP003 (SEQ ID NO:3) and the PD-L1 antibody exerted a similar effect and modestly improved the survival of tumor-bearing mice. As shown in FIG. 7b, and graphs 720, 722, 724, and 726 therein, depicting tumor growth curves of individual mice in each group, 90% of the mice in the saline group had died by day 17. By contrast, only 20% of the mice in the CLP002 (SEQ ID NO:2) group were dead by day 17. Eight mice showed a response to the CLP002 (SEQ ID NO:2) treatment, which is better than PD-L1 antibody treated mice (60% response). For CLP003 (SEQ ID NO:3), though only one mouse died on day 17, other mice experienced a rapid tumor progression.

The data in Examples 1-7 show that four identified peptides exhibited high and specific affinity to PD-L1. Particularly, the peptides CLP002 (SEQ ID NO:2) and CLP003 (SEQ ID NO:3) exhibited high blocking efficacy against the PD-1/PD-L1 interaction on recombinant PD-L1 protein and PD-L1-expressing tumor cells (Examples 3 and 4). The docking results confirmed that both CLP002 (SEQ ID NO:2) and CLP003 (SEQ ID NO:3) peptides blockade the PD-1/PD-L1 interaction. The binding site of CLP002 (SEQ ID NO:2) is extensively overlapped with the PD-1/PD-L1 binding residues, which explains why CLP002 (SEQ ID NO:2) competes with PD-1 for the PD-L1 binding and blocks the interaction.

In the animal study, we used an anti-mouse PD-L1 antibody (10F.9G2), which has been widely used as the PD-L1 inhibitor in various animal studies, as a positive control. Consistent with a previous report, mice treated with the PD-L1 antibody showed a slower tumor growth rate. Similarly, the CLP002 (SEQ ID NO:2) peptide also inhibited tumor growth in the mice (Example 6). Considering the fact that the CLP002 (SEQ ID NO:2) peptide was screened against human PD-L1 protein, which only exhibits 76% sequence identity with mouse PD-L1 protein, the antitumor activity of the CLP002 (SEQ ID NO:2) peptide in a mouse model implanted with mouse tumor cells is remarkable. The peptide inhibitor also prolonged the survival of the tumor-bearing mice compared to either the saline-treated mice or the antibody-treated mice (Example 7). It is notable that the dose of the anti-PD-L1 peptides (2 mg/Kg daily) is lower than that of the anti-mouse PD-L1 antibody (10 mg/Kg every other day). These results may indicate that the SEQ ID NO:2 peptide is more efficient than the antibody in inducing anti-tumor immune response.

Example 8: Evaluation of Peptides of SEQ ID NOs:5-7

In this Example, various properties of the peptides of SEQ ID NO:5, SEQ ID NO:6 and SEQ ID NO:7 were evaluated. The procedures for generating these values are described above in the beginning of the Examples section. The resulting data from these analyses can be found in Tables 4 and 5 below.

TABLE 4

Various Properties of Peptides of SEQ ID NOs: 5-7

| Name | $IC_{50}$ (ELISA) hPD-L1 | % Blocking efficiency at 10 µM (ELISA) hPD-L1 | IC50 (ELISA) mPD-L1 | % Blocking efficiency at 10 µM (ELISA) mPD-L1 | $IC_{50}$ (Competitive SPR) hPD-L1 | % Blocking efficiency at 10 µM (Competitive SPR) hPD-L1 | Half-life in 50% Human serum | % cell viability after incubation with 50 µM peptide |
|---|---|---|---|---|---|---|---|---|
| CLP2C14 (SEQ ID NO: 5) | 0.18 µM | 75.0 | 0.55 µM | 89.3 | 0.119 µM | 86.8 | 38.1 min. | ~100 |
| CLP2C21 (SEQ ID NO: 6) | 0.44 µM | 85.9 | 0.46 µM | 82.6 | 0.143 µM | 99.4 | 70.8 min. | ~100 |
| CLP2TR3 (SEQ ID NO: 7) | | 80 | | | | | 15 min. | |

TABLE 5

Additional Various Properties of Peptides of SEQ ID NOs: 5-7

| Name | $K_D$ (nM) to PD-L1 | $K_D$ (nM) to BSA | IC50 (nM) against the PD1/PD-L1 | % Blocking efficiency at 10 µM |
|---|---|---|---|---|
| CLP2C14 (SEQ ID NO: 5) | 2.78 nM | 408 nM | 5 nM | 75 |
| CLP2C21 (SEQ ID NO: 6) | 124 nM | 1235 nM | 6 nM | 78 |
| CLP2TR3 (SEQ ID NO: 7) | 258 nM | 2053 nM | | 80 |

This disclosure has been described in detail with particular reference to specific aspects thereof, but it will be understood that variations and modifications can be made within the spirit and scope of this disclosure.

What is claimed is:

1. A composition, comprising:
a therapeutic agent, the therapeutic agent comprising a polypeptide that comprises one or more amino acid sequences selected from the group consisting of:
SEQ ID NO: 2;
SEQ ID NO:5, wherein a disulfide bond is present between the cysteine amino acids at positions 1 and 12 of SEQ ID NO:5; and
SEQ ID NO:7.

2. The composition of claim 1, wherein the polypeptide comprises L-amino acids.

3. The composition of claim 1, wherein the polypeptide comprises one or more D- amino acids.

4. The composition of claim 1, wherein the polypeptide comprises a single copy of one of the sequences of SEQ ID NOs: 2, 5, or 7.

5. The composition of claim 1, wherein the polypeptide exhibits an equilibrium dissociation constant KD value against recombinant human PD-L1 that is less than about 300 nM, or of from about 0.1 nM to about 300 nM.

6. A composition, comprising:
a recombinant polypeptide, wherein the polypeptide exhibits at least 90% sequence identity to one or more amino acid sequences selected from the group consisting of:
SEQ ID NO: 2;
SEQ ID NO:5, wherein a disulfide bond is present between the cysteine amino acids at positions 1 and 12 of SEQ ID NO:5; and
SEQ ID NO:7.

7. The composition of claim 6, wherein the polypeptide exhibits at least 95% sequence identity to one or more amino acid sequences selected from the group consisting of:
SEQ ID NO: 2;
SEQ ID NO:5, wherein a disulfide bond is present between the cysteine amino acids at positions 1 and 12 of SEQ ID NO:5; and
SEQ ID NO:7.

8. The composition of claim 6, wherein the polypeptide exhibits at least 99% sequence identity to one or more amino acid sequences selected from the group consisting of:
SEQ ID NO: 2;
SEQ ID NO:5, wherein a disulfide bond is present between the cysteine amino acids at positions 1 and 12 of SEQ ID NO:5; and
SEQ ID NO:7.

9. The composition of claim 6, wherein the polypeptide comprises L-amino acids.

10. The composition of claim 6, wherein the polypeptide comprises one or more D- amino acids.

11. The composition of claim 6, wherein the polypeptide comprises a single copy of one of the sequences of SEQ ID NOS: 2, 5, or 7.

12. A method of treating PD-L1 expressing cancer in a mammalian subject in need of treatment, comprising:
administering to a subject a therapeutically effective amount of a therapeutic agent, the therapeutic agent comprising a polypeptide that comprises one or more amino acid sequences selected from the group consisting of:
SEQ ID NO: 2;
SEQ ID NO:5, wherein a disulfide bond is present between the cysteine amino acids at positions 1 and 12 of SEQ ID NO:5; and
SEQ ID NO:7.

13. The method of claim 12, wherein the therapeutic agent comprises at least two amino acid sequences selected from the group consisting of:
SEQ ID NO: 2;
SEQ ID NO:5, wherein a disulfide bond is present between the cysteine amino acids at positions 1 and 12 of SEQ ID NO:5; and
SEQ ID NO:7.

14. The method of claim 12, wherein the polypeptide comprises a single copy of one of the sequences of SEQ ID NOs: 2, 5, or 7.

15. The method of claim 12, wherein the polypeptide comprises L- amino acids.

16. The method of claim 12, wherein the polypeptide comprises one or more D- amino acids.

* * * * *